US011377402B2

(12) United States Patent
Dorsi et al.

(10) Patent No.: US 11,377,402 B2
(45) Date of Patent: Jul. 5, 2022

(54) INTEGRATED AROMATICS FORMATION AND METHYLATION

(71) Applicant: ExxonMobil Chemical Patents Inc., Baytown, TX (US)

(72) Inventors: Catherine M. Dorsi, Houston, TX (US); Todd E. Detjen, Bellaire, TX (US); Mayank Shekhar, Houston, TX (US); Anthony Go, Houston, TX (US)

(73) Assignee: ExxonMobil Chemical Patents Inc., Baytown, TX (US)

( * ) Notice: Subject to any disclaimer, the term of this patent is extended or adjusted under 35 U.S.C. 154(b) by 223 days.

(21) Appl. No.: 16/605,387

(22) PCT Filed: Apr. 19, 2018

(86) PCT No.: PCT/US2018/028234
§ 371 (c)(1),
(2) Date: Oct. 15, 2019

(87) PCT Pub. No.: WO2018/217337
PCT Pub. Date: Nov. 29, 2018

(65) Prior Publication Data
US 2021/0122688 A1     Apr. 29, 2021

Related U.S. Application Data

(60) Provisional application No. 62/509,385, filed on May 22, 2017.

(30) Foreign Application Priority Data

Jun. 28, 2017  (EP) .................................. 17178344

(51) Int. Cl.
*C07C 7/08*     (2006.01)
*C07C 2/86*     (2006.01)
(Continued)

(52) U.S. Cl.
CPC ................ *C07C 7/08* (2013.01); *C07C 2/864* (2013.01); *C07C 2/865* (2013.01); *C07C 5/2737* (2013.01);
(Continued)

(58) Field of Classification Search
CPC ......... C07C 7/08; C07C 29/48; C07C 5/2737; C07C 31/04; C07C 15/08; C07C 15/073; C07C 15/04; C07C 2/02
See application file for complete search history.

(56) References Cited

U.S. PATENT DOCUMENTS 2,659,763 A * 11/1953 Humphreys ............ C07C 15/08
585/816
4,642,402 A *  2/1987 Jensen ...................... C07C 2/00
585/411
(Continued)

FOREIGN PATENT DOCUMENTS

WO        2017052858        3/2017

OTHER PUBLICATIONS

Sinnott ("2.14 Recycle Processes." Chemical Engineering Design, Fourth ed. vol. 6, 2005, 50) (Year: 2005).*

*Primary Examiner* — Youngsul Jeong
*Assistant Examiner* — Jason Y Chong

(57) ABSTRACT

Systems and methods are provided for integration of an aromatic formation process for converting non-aromatic hydrocarbon to an aromatic product and subsequent methylating of a portion of the aromatic product to produce a methylated product, with improvements in the aromatic formation process and/or the methylation process based on integrating portions of the secondary processing trains associated with the aromatic formation process and the methylation process. The aromatic formation process and methylation process can be used, for example, for integrated (Continued)

production of specialty aromatics or gasoline blending components.

26 Claims, 5 Drawing Sheets

(51) Int. Cl.
    *C07C 2/76*     (2006.01)
    *C07C 5/27*     (2006.01)
    *C07C 29/48*     (2006.01)
    *C07C 15/04*     (2006.01)
    *C07C 15/073*     (2006.01)
    *C07C 15/08*     (2006.01)
    *C07C 31/04*     (2006.01)

(52) U.S. Cl.
    CPC .............. *C07C 29/48* (2013.01); *C07C 15/04* (2013.01); *C07C 15/073* (2013.01); *C07C 15/08* (2013.01); *C07C 31/04* (2013.01)

(56) References Cited

U.S. PATENT DOCUMENTS

| | | | | |
|---|---|---|---|---|
| 5,043,502 | A * | 8/1991 | Martindale | C07C 15/067 585/323 |
| 9,416,072 | B1 * | 8/2016 | Chen | C07C 7/163 |
| 2006/0235088 | A1 * | 10/2006 | Olah | C07C 29/50 518/702 |
| 2014/0275674 | A1 * | 9/2014 | Verma | C07C 7/167 585/259 |
| 2015/0376087 | A1 | 12/2015 | Molinier et al. | |
| 2016/0060187 | A1 * | 3/2016 | Kendall | C07C 7/14 585/454 |

* cited by examiner

INTEGRATED AROMATICS FORMATION AND METHYLATION

CROSS-REFERENCE OF RELATED APPLICATIONS

This application is a National Phase Application of PCT Application PCT/US2018/028234 filed Apr. 19, 2018, which claims priority to and the benefit of U.S. Provisional Application No. 62/509,385, filed May 22, 2017 and of European Patent Application No. 17178344.2, filed Jun. 28, 2017, which are incorporated by reference in their entirety.

FIELD OF THE INVENTION

The invention relates to hydrocarbon aromatization and aromatic hydrocarbon methylation, to systems and methods for integrating the aromatization and methylation, e.g., by integrating (i) the conversion of non-aromatic hydrocarbon to aromatic hydrocarbon with (ii) the methylation of the aromatic hydrocarbon. The invention also relates to apparatus useful in such systems and methods, and to the use of the methylated aromatic hydrocarbon.

BACKGROUND OF THE INVENTION

Conversion of aliphatic compounds to aromatic hydrocarbon ("aromatics") is an ongoing area of study for chemical manufacture. Certain aromatic compounds, such as para-xylene, have a relatively high commercial value. Processes that can allow formation of aromatics from feed streams that primarily have fuel value, such as natural gas, natural gas liquids, or fuel gas, can be beneficial if the conversion to aromatics can be performed at a reasonable cost. Due to the relatively low activity of alkane compounds in processes for direct conversion to aromatics, additional improvements in processes for conversion of alkane to aromatics are desirable.

In addition to conversion of non-aromatic hydrocarbon to aromatics, production of para-xylene in commercially desirable amounts can also involve subsequent alkylation of aromatics. In particular, a methylation process can be used to convert benzene and/or toluene into xylenes. While methylation can be effective for production of xylenes, the methylation step corresponds to a second, separate reactor for production of xylene that can also require a second processing train for separation and recovery of the various hydrocarbon products generated in an alkylation reaction environment.

U.S. Pat. No. 5,043,502 describes a method for dehydroaromatization of $C_2$-$C_5$ aliphatic hydrocarbons to form aromatics. Para-xylene is produced both from the dehydroaromatization reaction and from subsequent methylation of toluene generated by the dehydroaromatization reaction. Benzene is also produced from dehydroaromatization and is described as being methylated to toluene during the subsequent methylation.

U.S. Patent Application Publication No. 2016/0060187 describes methods for treating off-gas produced in the production of para-xylene by the alkylation of benzene and/or toluene with methanol. The treated off-gas stream, which contains $C_{4-}$ hydrocarbons, may be further processed in an olefins plant/process to yield valuable light alkanes and olefins.

U.S. Patent Application Publication No. 2015/0376087 describes methods for the production of para-xylene. The methods include methylation of benzene and/or toluene to form a methylated effluent, recovery of para-xylene from the methylated effluent to produce a para-xylene depleted stream, and isomerization of portions of the para-xylene depleted stream under liquid phase and/or vapor phase conditions to form additional xylenes for eventual recovery. Even with these advances, increases in the demand for para-xylene and related compounds has led to a need for improved processes for formation of para-xylene.

SUMMARY OF THE INVENTION

The invention concerns processes which include (a) an aromatic formation process for converting non-aromatic hydrocarbon to an aromatic product containing para-xylene and (b) methylating at least a portion of the aromatic product to produce a methylated product containing additional para-xylene, with the aromatic product and the methylated product being maintained as separate products prior to separation of para-xylene. Alternatively, the invention concerns processes which include (a) an aromatic formation process for converting non-aromatic hydrocarbon to an aromatic product containing toluene and (b) methylating a portion of the aromatic product to produce a methylated product containing additional toluene. The invention relates in part to the discovery that improvements can be made to the aromatic formation process and/or the methylation process by integrating portions of the secondary processing trains associated with the aromatic formation process and the methylation process.

More particularly, benefits can be achieved by integration of the light ends processing trains from aromatic formation and methylation. The light ends from an aromatic formation process and a methylation process are qualitatively different, as opposed to the qualitative similarities in the $C_8$ fractions produced from these processes. Based on product composition, it would be expected that combining the qualitatively similar $C_8$ fractions from aromatic formation and from methylation could allow for process improvements, while the qualitatively different light ends fractions would be separately processed. It has surprisingly been discovered that even though the qualitatively similar $C_8$ fractions should be separately handled, the qualitatively dissimilar light ends can be at least partially processed together. This can facilitate recycle of non-aromatic hydrocarbons from both the aromatic formation process and the methylation process as part of the feed to the aromatic formation process. This is in contrast to conventional methylation processes, where the light ends fractions from methylation are processed and used as a feed for an olefins plant. Due to the low conversion rate of many aromatic formation processes, recycle of non-aromatic hydrocarbons can improve the overall process yield. Combining at least a portion of the light ends processing train from the aromatic formation process with the light ends processing train from the methylation process can allow the non-aromatic hydrocarbons from methylation to also be included as part of the recycled non-aromatic hydrocarbons to the aromatic formation process. In particular, it can be beneficial to combine the light ends processing train from the aromatic formation process after the removal of dimethyl ether in the light ends processing train from the methylation process, so as to avoid introduction of unexpected oxygenates into the aromatic formation process.

Other aspects relate to integrating the aromatic formation process and the methylation process by integration of cooling systems. Conventionally, processes such as methylation and/or xylene separation have been structured to avoid the need for use of a $C_2$ refrigerant (such as ethylene) due in part to the additional equipment footprint and costs. However, because methane is not consumed and/or is consumed in only modest amounts in some types of aromatic formation processes, heat exchange with a $C_2$ refrigerant may be included in the light ends processing train to allow for demethanization, so that recycle of methane to the aromatic formation process is reduced or minimized. For example, it has been found that it can be efficient to increase the amount of available $C_2$ refrigeration so that it can be used in other separations, such as the light ends processing train for the methylation process and/or separation of para-xylene by crystallization. More generally, a cooling system based on use of one or more $C_1$-$C_4$ refrigerants for separation of an aromatics formation effluent may be expanded to allow the same cooling system to also provide refrigerant for other separations. For example, a $C_2$ refrigeration system used for the aromatics formation process may be associated with a $C_3$ refrigeration system for additional cooling of the $C_2$ refrigerant. In such an aspect, the amount of $C_2$ refrigeration and/or the amount of $C_3$ refrigeration can be increased to allow the $C_2$ and/or $C_3$ refrigerant to be used for separations in the light ends processing train of the methylation process.

In still other particular aspects, hydrogen generated during aromatic formation can be used for saturation of olefins generated during a methylation process. For example, during separation of $C_8$ aromatics using adsorbent beds, styrene can be an undesirable contaminant. Aromatic compounds with unsaturated alkyl side-chains, such as styrene, can be removed from a feed stream for separation of $C_8$ aromatics by exposing the feed stream to hydrogen in the presence of an olefin saturation catalyst. It has been discovered that hydrogen separated from an aromatic formation effluent derived from a process based on conversion of small alkanes can provide the hydrogen for such olefin saturation.

DETAILED DESCRIPTION OF THE EMBODIMENTS

Figure 1:
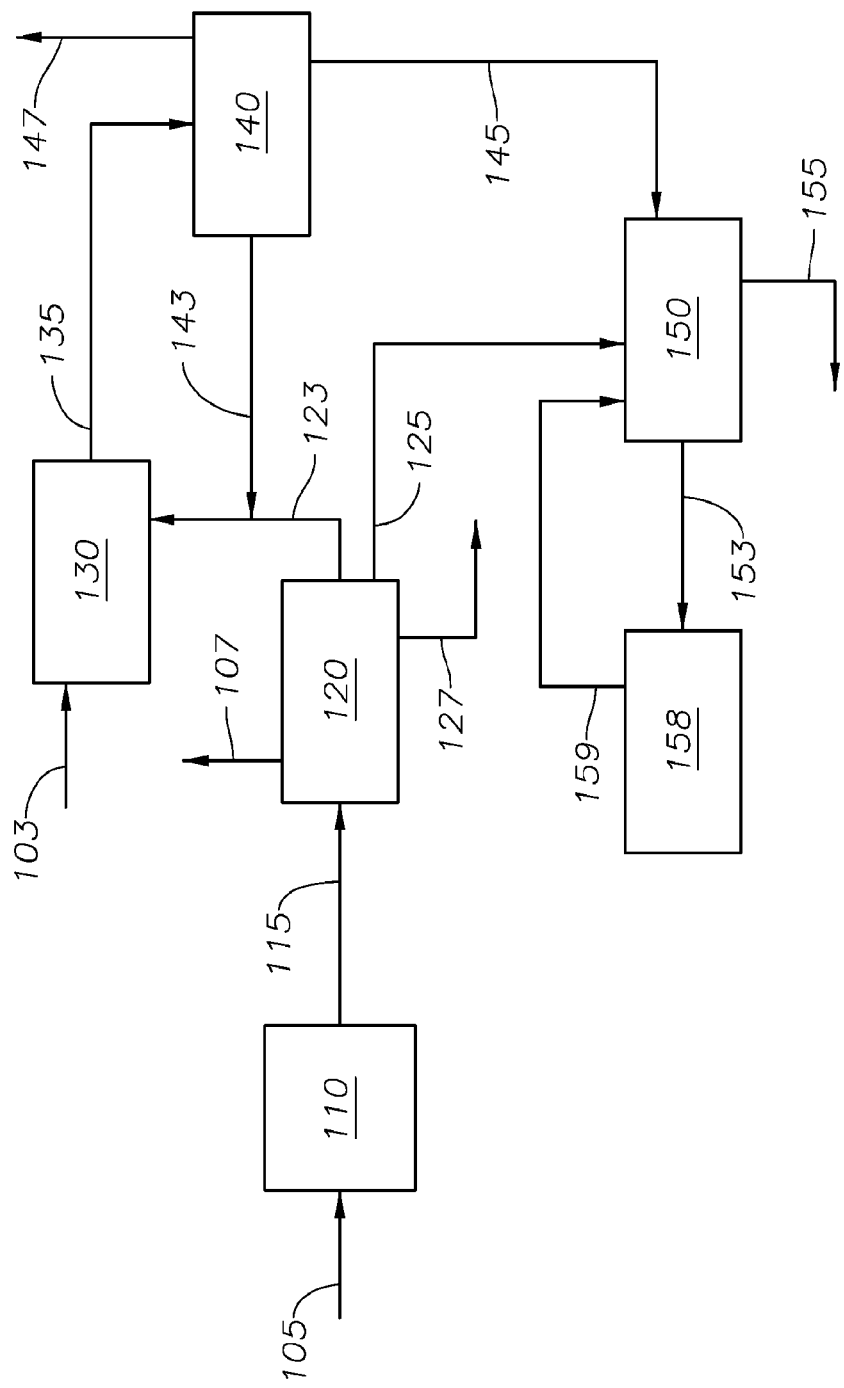
FIG. 1 schematically shows an example of a system for converting a feed to form aromatic hydrocarbon combined with a methylation process to produce a para-xylene product.

In various aspects, systems and methods are provided for production of para-xylene using integrated processes for aromatic formation (i.e., conversion of non-aromatic hydrocarbon to form aromatics) and methylation of the converted aromatics. Certain aspects of the invention are based on the discovery that reduction in equipment footprint, complexity, and/or costs can be achieved by integration of the off-gas processing trains of the aromatic formation process and the methylation process. In some aspects, this can correspond to a selective integration, so that the $C_8$ products generated from aromatic formation and methylation can remain distinct while at least a portion of the processing of secondary products is integrated. For example, this can correspond to integration of off-gas processing trains during aromatics production.

Although both the aromatic formation process and the methylation process can generate similar product streams (e.g., a $C_8$ aromatics stream, a $C_6$-$C_7$ product stream, etc.), in various aspects different separation processes are employed for separation of the methylation effluent and the aromatic formation effluent. Although the methylation effluent and the aromatic formation effluent can have substantially the same ratios of $C_8$ products in the respective $C_8$ aromatics streams, more typically the $C_8$ aromatics streams produced from the aromatic formation process and the methylation process will have different compositions. This can include differences in both the concentration of para-xylene and the concentration of ethylbenzene. If the $C_8$ aromatics streams from an aromatics formation process and a methylation process are combined prior to any para-xylene recovery, any subsequent para-xylene recovery stage will be limited to performing xylene recovery on a stream that includes an average of the para-xylene contents of the combined streams. As an alternative, if the $C_8$ aromatics streams are maintained as separate streams prior to introduction of at least one stream into a para-xylene recovery stage, the differences in the concentration of para-xylene between $C_8$ aromatics streams can be exploited to provide an improved para-xylene separation process. Thus, it can be beneficial for streams having a greater para-xylene concentration, e.g., the $C_8$ aromatics stream derived from a methylation process, to be kept segregated from streams having a lesser para-xylene concentration, e.g., the $C_8$ aromatics stream derived from an aromatics formation process. For example, for separation stages based on a simulated moving bed, it can be beneficial to introduce streams having different para-xylene concentrations at different locations in the simulated moving bed. Maintaining segregation between streams with different para-xylene concentrations until one of the streams has at least partially passed through a para-xylene recovery stage has been found to beneficially (i) increase the efficiency of para-xylene separation, (ii) increase para-xylene yield, and/or (iii) decrease the size, capacity, and/or complexity of the xylene separation stages and zones compared to separations that are carried out with the streams combined.

Conventionally, because of the benefits of maintaining the separate status of the primary aromatic products from aromatic formation and methylation during para-xylene production, the separation of the remaining by-product portions of these effluents has also been performed separately. More generally, conventional methylation processes typically involve processing of light ends for use as a feed to an olefin plant, based in part on the presence of olefins in the methylation effluent. This can be in contrast to aromatics formation processes for conversion of $C_2$-$C_5$ alkanes to aromatics, where the light ends generated from the process typically contain a small or minimal amount of olefins. In spite of the qualitative differences between the off-gas streams from some aromatic formation processes and methylation processes, it has been discovered that integration of processing of these qualitatively distinct off-gas streams can be beneficial.

Based in part on the low single-pass yield of various aromatic formation processes, such as aromatic formation processes based on conversion of $C_2$-$C_5$ alkanes, it can be desirable to recycle non-aromatic by-products from an aromatic formation process for use as part of the feed to the aromatic formation process. This can improve overall yield on the non-aromatic hydrocarbon feed to the aromatic formation process. When an aromatic formation process and a methylation process are used in combination to provide an integrated process for production of, for example, para-xylene or toluene, it can also be beneficial to recycle non-aromatic by-products from the methylation process to the aromatic formation process. It has been unexpectedly discovered that, after optional initial processing, portions of the secondary product effluent from aromatics formation can be combined with the secondary product effluent from methylation. It has also been discovered that, after optional initial processing, it can be efficient to combine portions of the secondary product effluent from methylation with the secondary product effluent from aromatics formation. By combining the process flows for processing of the secondary product effluents from an aromatic formation process and a methylation process, equipment footprint can be reduced or minimized while still recovering and recycling non-aromatic hydrocarbon from the secondary product effluents. For example, instead of attempting to separate olefins from paraffins in a $C_2$-$C_3$ by-product stream from methylation for use in an olefin plant, both the paraffins and olefins from a $C_2$-$C_3$ by-product stream can be added to light ends from an aromatic formation process to form a recycled portion of the feed to the aromatic formation process.

Additional efficiencies can be derived from thermal integration, and in particular the integration of cooling systems associated with different processes. An aromatics formation process can generate a primary product effluent that includes aromatics and a secondary product effluent that includes a variety of lower boiling compounds, such as alkanes, olefins, oxygenates, hydrogen, carbon oxides, and/or other non-aromatic hydrocarbons. It can be beneficial to perform a separation on the secondary product effluent to separate a fraction including methane from a fraction including other types of hydrocarbon (i.e., $C_{2+}$ hydrocarbon). Such a $C_{2+}$ stream can be used, for example, as a recycle stream to an aromatics formation process. For example, separating methane from other aliphatic hydrocarbons can be beneficial for aromatic formation processes that convert less than 10 wt. % of methane (relative to the weight of methane in the aromatic formation feed) during a single pass, or less than 5 wt. % or less than 2 wt. %. One option for performing such a demethanation process can be to use a distillation tower that includes ethylene (i.e., a $C_2$ refrigerant) for heat exchangers in the process. The ethylene refrigerant circulation system can also be used to improve other types of separations, such as using ethylene refrigerant for separation of the secondary product effluent from methylation and/or as a refrigerant for crystallization of para-xylene. Additionally, or alternately, a cooling system may include multiple refrigerants, such as a cooling system that includes both a $C_2$ refrigerant and a $C_3$ refrigerant. In such aspects, either the $C_2$ refrigerant or the $C_3$ refrigerant may be used to improve other types of separations. More generally, a cooling system can include $C_1$-$C_4$ refrigerant(s) for use in providing cooling for separation of an aromatics formation effluent. One or more of such $C_1$-$C_4$ refrigerant(s) may be used to improve other types of separations.

For the purpose of this description and appended claims, the following terms are defined. The term "$C_n$" hydrocarbon wherein n is a positive integer, means a hydrocarbon having n number of carbon atom(s) per molecule. Of course, different types of hydrocarbons can have various numbers of hydrogens while having the same number of carbon atoms. The terms "$C_{n+}$" hydrocarbon and "$C_{n-}$" hydrocarbon, wherein n is a positive integer, mean a hydrocarbon having at least n number of carbon atom(s) per molecule or no more than n number of carbon atom(s) per molecule, respectively. The terms "aromatics" and "aromatic hydrocarbon" mean hydrocarbon molecules containing at least one aromatic core. The term "hydrocarbon" encompasses mixtures of hydrocarbon, including those having different values of n. The term "organic oxygenate" means molecules (including mixtures of molecules) having the formula $C_nH_{2n+1}OC_mH_{2m+1}$, wherein C, H and O are carbon, hydrogen and oxygen, respectively; n is an integer having a value ≥1, e.g., in the range of from 1 to 4; and m is an integer having a value ≥zero, e.g., in the range of from zero to 4. Examples of organic oxygenate include one or more of methanol, ethanol, dimethyl ether, and diethyl ether. The term "syngas" means a mixture comprising ≥12 mole % molecular hydrogen and ≥0.4 mole % carbon monoxide, the mole percents being per mole of the mixture.

In this description and appended claims, reference may be made to aromatics streams or fractions, e.g., those described as a $C_6$ aromatics stream or fraction, a $C_7$ aromatics stream or fraction, a $C_6$-$C_7$ aromatics stream or fraction, a $C_8$ aromatics stream or fraction, a $C_7$-$C_8$ aromatics stream or fraction, or a $C_{9+}$ aromatics stream or fraction. Each of such streams or fractions is defined to have a concentration of the named aromatic component(s) of at least 50 wt. %. Thus, a $C_6$ aromatics stream is defined herein as a stream containing at least 50 wt. % of $C_6$ aromatic compounds. Optionally, the concentration of the named aromatic component(s) can be at least 75 wt. % or at least 90 wt. %.

Processes for conversion of alkane to aromatic hydrocarbon are generally characterized as direct or indirect. Direct conversion processes are those where the alkane-containing feed is introduced into the reaction environment where aromatic hydrocarbon is formed from non-aromatic hydrocarbon. Indirect conversion processes are those where the alkane-containing feed is introduced into a reaction stage different from the reaction stage where aromatic hydrocarbon is formed. For example, a reaction scheme for first converting methane to methanol and then feeding the methanol into a reaction for aromatic formation corresponds to an indirect conversion process. It is noted that a reaction scheme could correspond to both a direct and an indirect conversion process if some aromatic hydrocarbon is formed in a first process that receives the alkane-containing feed while additional aromatic hydrocarbon is formed in a second process that receives an effluent from the first process as a feed. It is noted that subsequent methylation of an existing aromatic feed does not correspond to a process for formation of aromatic hydrocarbon from non-aromatic hydrocarbon.

As used herein, an "aromatic formation" process refers to one or more processes that are used to convert non-aromatic hydrocarbon, e.g., aliphatic hydrocarbon to aromatic hydrocarbon, optionally in the presence of other components and/or co-feeds. An aromatic formation process based on a direct conversion process may encompass those having only one reactor and/or reaction stage (although multiple stages could be included). An aromatic formation process based on an indirect conversion process will typically include multiple process stages or reaction environments, since the reaction for initial conversion of the alkane occurs in a different reaction environment than the reaction for aromatic formation.

As used herein, the numbering scheme for the groups of the Periodic Table of the Elements is as disclosed in Chemical and Engineering News, 63(5), 27 (1985).

Integration of Aromatics Formation and Methylation Processes

An example of a system for using an aromatics formation process and a methylation process to facilitate para-xylene production and separation is schematically shown in FIG. 1. A suitable feed for aromatics formation is introduced via conduit 105 into an aromatic formation process 110. Effluent 115 from aromatic formation process 110 is then passed into a first separation process 120, which separates at least fractions 123 and 125 from effluent 115. Fraction 125 contains at least a portion of the $C_8$ aromatic hydrocarbon from effluent 115 and fraction 123 contains at least a portion of the benzene and $C_7$ aromatic hydrocarbon from effluent 115. A lower boiling (including unconverted) fraction 107 can also be separated from effluent 115 and optionally returned (at least in part) to the aromatic formation process 110. Optionally, a stream 127 is separated from effluent 115 in first separation process 120. Stream 127 can comprise, e.g., at least a portion of any $C_{9+}$ hydrocarbons in effluent 115. In certain aspects, stream 127 comprises a majority (e.g., ≥90 wt. %) of what remains of the effluent after the separation of fractions 123, 125, and/or 107. Fraction 123 is introduced into a methylation process 130 along with a methylating agent feed 103 (e.g., methanol) to produce $C_8$ aromatic hydrocarbon by methylating at least a portion of the benzene and/or $C_7$ aromatic hydrocarbon in fraction 123. The effluent 135 from the methylation process 130 is conducted to a second separation process 140 to separate at least fractions 143, 145, and 147 from methylation effluent 135. Fraction 145 contains at least a portion of the $C_8$ aromatic hydrocarbon from effluent 135, and fraction 143 contains at least a portion of the benzene and $C_7$ aromatic hydrocarbon from effluent 135. Fraction 147 contains at least a portion of the $C_{5-}$ (i.e., aliphatic hydrocarbons and other light ends) from effluent 135. In various aspects, at least a portion of fraction 147 can be used as part of the feed for aromatic formation process 110. Fractions 125 and 145 are passed to the third separation process 150 for separation of para-xylene from other $C_8$ aromatic hydrocarbon. In third separation process 150, a stream 155 enriched in para-xylene and a stream 153 depleted in para-xylene (relative to the paraxylene content of stream 145) are separated from fractions 125 and 145. Stream 153, which is depleted in para-xylene, is passed into isomerization process 158 for conversion of ortho- and meta-xylene into para-xylene. The resulting effluent stream 159 with an increased amount of para-xylene relative to stream 153 is returned to the third separation process 150 for separation of the para-xylene. Optionally, stream 159 can be introduced into the third separation process 150 at a different separation stage than the input separation stage for stream 125, which can allow the third separation process 150 to take advantage of differing concentrations of para-xylene in stream 159 and 125. For example, a stream having a higher para-xylene concentration can be introduced into separation process 150 at a later separation stage. This can allow earlier separation processes to have a smaller processing capacity. Since the earlier separation stages in a separator correspond to stages with the largest volume (i.e., due to lower concentration of the separation target), reducing the input flows to early separation stages can beneficially reduce the size of the potentially largest stages within a multi-stage separator. Optionally, stream 145 can be introduced into the third separation process 150 at a different stage than the input stage(s) for stream 125 and stream 159, which can allow the third separation process 150 to take advantage of differing concentrations of para-xylene in streams 125, 145, and/or 159.

Alternatively, at least a portion of effluent 135 can be conducted to separation process 120, for separating streams 143 and/or 145. In other words, at least part of the separation functionality of second separation process 140 can be carried out in first separation process 120. In still another alternative, at least a portion of effluent 115 can be conducted to second separation process 140.

It is noted that a configuration similar to FIG. 1 can alternatively be used for production of toluene, such as toluene for use as a gasoline blending component. In such a configuration, fractions 125 and 145 can correspond to $C_7$ product streams and/or $C_7$-$C_8$ product streams. In such a configuration, xylene separation stage 150 and xylene isomerization stage 158 can be omitted. For example, effluent 115 from aromatic formation process 110 can be passed into a first separation process 120, which separates at least fractions 123 and 125 from effluent 115. In a configuration for toluene production, fraction 125 contains at least a portion of the $C_7$ aromatic hydrocarbon from effluent 115 and fraction 123 contains at least a portion of the $C_6$ aromatic hydrocarbon (benzene) from effluent 115. A lower boiling (including unconverted) fraction 107 can also be separated from effluent 115 and optionally returned (at least in part) to the aromatic formation process 110. Optionally, a stream 127 is separated from effluent 115 in first separation process 120. Stream 127 can comprise, e.g., at least a portion of any $C_{9+}$ hydrocarbons in effluent 115. It is noted that during production of toluene for use as a gasoline blending component, any $C_8$ aromatics produced can also correspond to useful blend components, so the $C_8$ components can be substantially included with fraction 125. Alternatively, if a higher purity $C_7$ fraction is desired, the $C_8$ components can be substantially included with stream 127. In certain aspects, stream 127 comprises what remains of the effluent after the separation of fractions 123, 125, and/or 107. Fraction 123 is introduced into a methylation process 130 along with a methylating agent feed 103 (e.g., methanol) to produce $C_7$ aromatic hydrocarbon by methylating at least a portion of the benzene in fraction 123. The effluent 135 from the methylation process 130 is conducted to a second separation process 140 to separate at least fractions 143, 145, and 147 from methylation effluent 135. Fraction 145 contains at least a portion of the $C_7$ aromatic hydrocarbon from effluent 135, and fraction 143 contains at least a portion of the benzene from effluent 135. Fraction 147 contains at least a portion of the $C_{5-}$ (i.e., aliphatic hydrocarbons and other light ends) from effluent 135. In various aspects, at least a portion of fraction 147 can be used as part of the feed for aromatic formation process 110.

Figure 2:
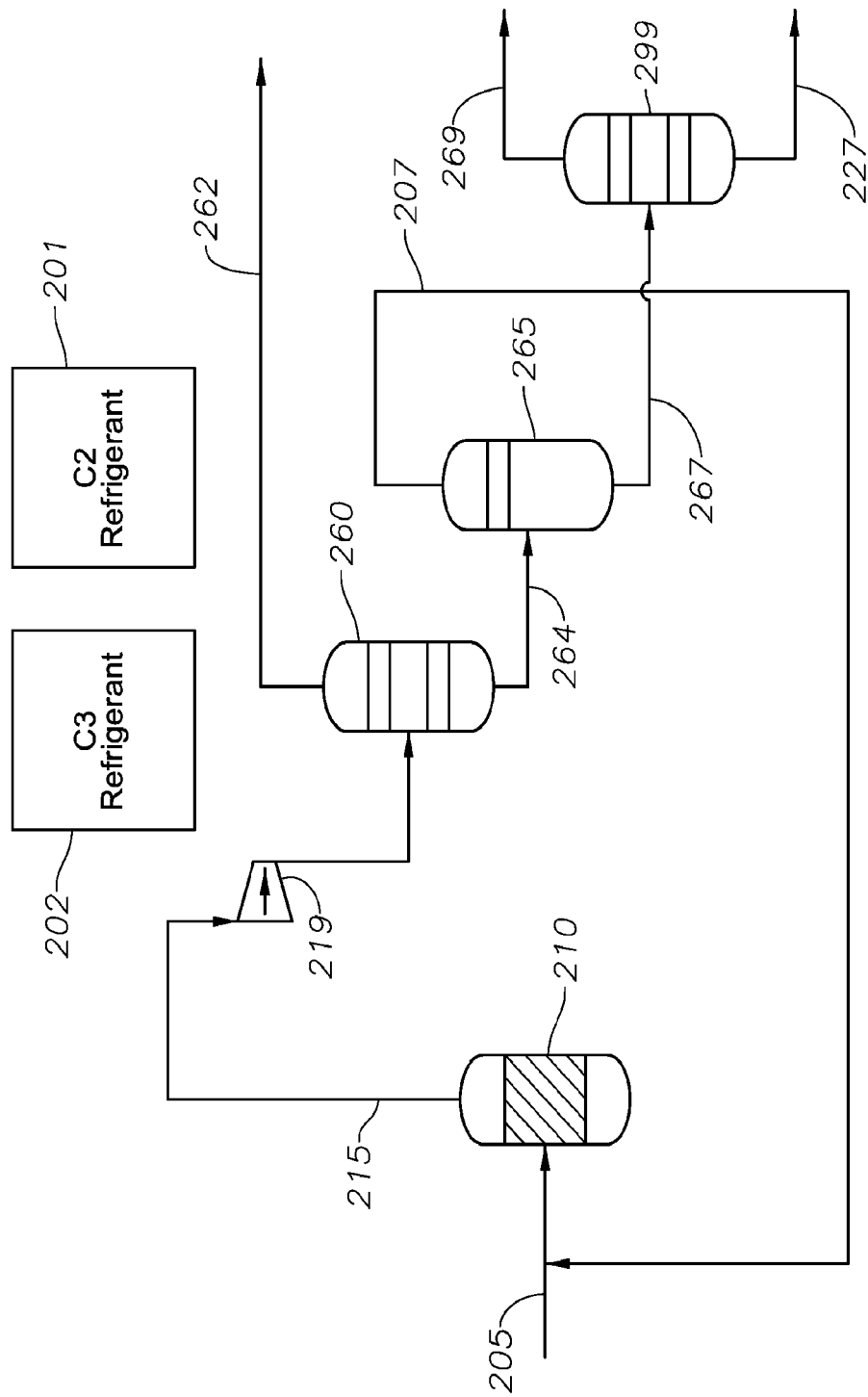
FIG. 2 schematically shows an example of a system for performing separations on an effluent from an aromatic formation process.

The process flow in FIG. 2 is an example of a more detailed view of the stages/processes that can be used to perform aromatics formation process 110 and first separation process 120 from FIG. 1. It is noted that similar numbers are used to denote similar elements between figures. In FIG. 2, a suitable feed 205, such as a feed containing ethane, is introduced into an aromatics formation process 210. An aromatics formation effluent 215 is formed, which can be passed through a series of separation stages as shown in FIG. 2 to perform the first separation process 120 shown in FIG. 1. Prior to and/or during the separation stages, compression of the aromatic formation effluent 215 using one or more compressors 219 may facilitate performing the various separations. In a first separation stage, corresponding to a demethanation stage 260, at least a $C_{2+}$ fraction 264 and a lower boiling fraction 262 can be separated from the aromatic formation effluent 215. The lower boiling fraction 262 can include methane, hydrogen, carbon oxides, and/or other compounds that have a lower boiling point than ethane/ethylene. In other words, lower boiling fraction 262 can correspond to a $C_{1-}$ stream. The $C_{2+}$ fraction 264 can then be passed into one or more additional separation stage(s). The demethanation stage can include one or more fractionation towers which utilize $C_2$ refrigeration system 201 for indirectly transferring heat in at least one heat exchanger. The heat exchangers using $C_2$ refrigerant 201 can be associated with additional heat exchangers which utilize $C_3$ refrigerant 202. FIG. 2 shows a depentanation stage 265 for separating a $C_2$-$C_5$ stream 207 and a $C_{6+}$ stream 267 from the $C_{2+}$ fraction 264. In other aspects, a separation stage with a different cut point could be used, such as a debutanation stage or a depropanation stage. Optionally, the ordering of the depentanation stage 265 and the demethanation stage 260 can be reversed. Preferably, the one or more additional separation stages can be used to provide a $C_{6+}$ stream 267. Optionally, but preferably, the $C_{6+}$ stream 267 can undergo further separation, such as separation in separation stage 299. In some aspects (such as aspects where para-xylene production is desired), $C_{6+}$ stream 267 can undergo separation to form a $C_{9+}$ stream 227 and a $C_6$-$C_8$ stream 269. The $C_6$-$C_7$ stream 269 can then be used, for example, to form fraction 123 and fraction 125 from FIG. 1. Alternatively, $C_{6+}$ stream 267 can undergo separation to form a $C_{8+}$ stream 227 and a $C_6$-$C_7$ stream 269. The $C_6$-$C_7$ stream 269 can then be used, for example, to form fraction 123 and fraction 125 from FIG. 1.

In FIG. 2, the demethanation stage 260 can correspond to a separation column with an associated refrigerated condensor. In some aspects, the cooling system (such as a system for providing cooling fluids to heat exchangers) can include ethylene as a refrigerant to provide a sufficiently cold temperature to improve the separation of methane from $C_2$ hydrocarbons. In order to operate a cooling system containing ethylene refrigerant, a propylene cooling system may be used to cool the ethylene refrigerant in a desired temperature and/or pressure operating range.

During a methylation process 130 (or other alkylation process), the product of a reaction between methanol and toluene and/or benzene is an alkylation effluent comprising para-xylene and other xylene isomers, water vapor, unreacted toluene and/or benzene, unreacted methanol, phenolic impurities, and a variety of light gas by-products, such as $C_{4-}$ hydrocarbons, including light olefins and contaminants such as nitrogen, nitrogen oxides, carbon monoxide, carbon dioxide, and oxygenates such as ethanal and dimethyl ether. The alkylation effluent will also generally contain some $C_{9+}$ aromatic by-products. In addition, where the process is conducted in a fluidized catalyst bed, the alkylation effluent will contain some entrained solid catalyst and catalyst fines. Thus, the effluent, which is generally in the vapor phase, leaving the (final) fluidized bed reactor is generally passed through an integral cyclone separator to remove some of the entrained catalyst solids and return them to the alkylation reactor.

Figure 3:
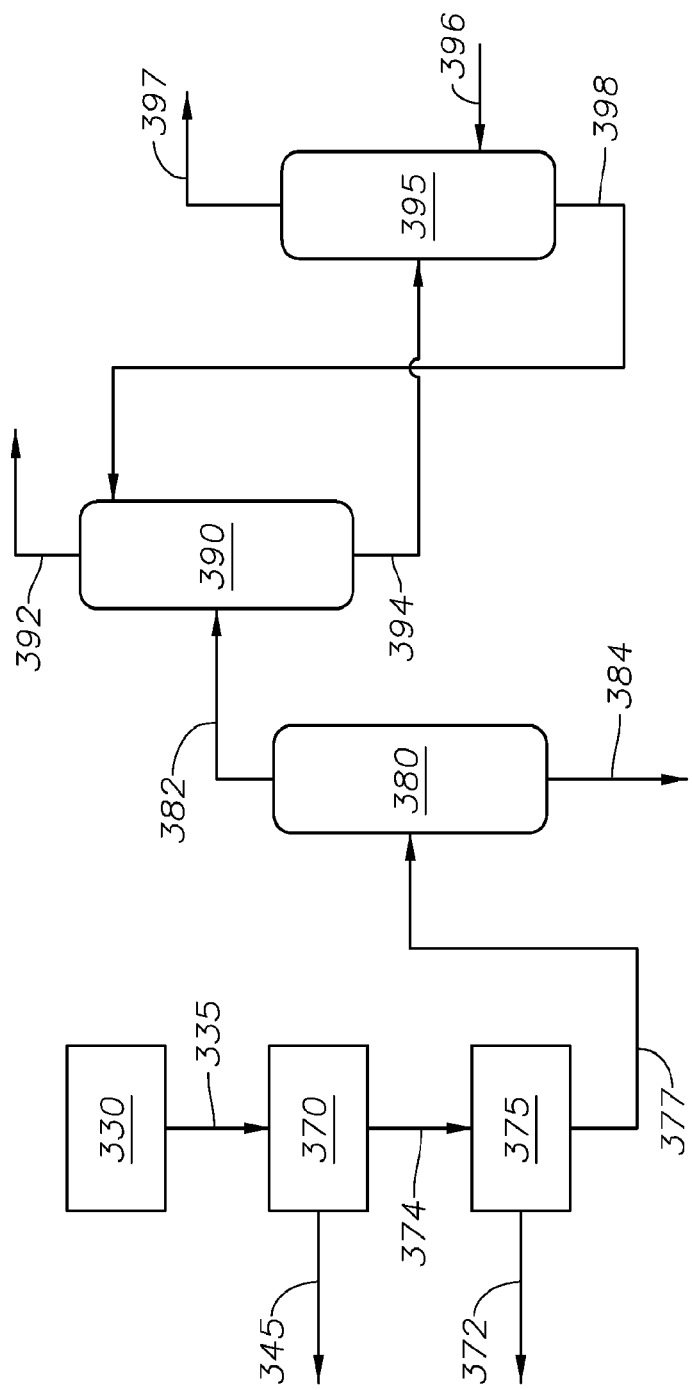
FIG. 3 schematically shows an example of a system for performing separations on an effluent from an alkylation process.

FIG. 3 schematically shows a more detailed view of stages and processes for carrying out methylation process 130 and second separation process 140 from FIG. 1.

Referring to FIG. 3, methylation process 330 (which can be substantially the same process as indicated by reference number 130 in FIG. 1) can generate a methylation effluent 335 that is fed to a separation process, such as second separation process 140 in FIG. 1. In FIG. 3, a series of separation stages represents the second separation process 140. A first fraction 345 containing xylenes and a second fraction 374 containing a by-product mixture can be separated from the alkylation effluent, typically using one or more fractionation columns 370. Further separations (not shown) to recover the unreacted methanol, unreacted benzene, and/or toluene (such as a fraction 143), heavy ($C_{9+}$) by-products and other by-products are possible and within the skill of one in the art. Para-xylene is recovered from the first fraction 345, typically by fractional crystallization or selective adsorption (not shown).

The second fraction 374, containing the light hydrocarbons, is treated by a treatment system 375 to recover at least the valuable olefinic component of the stream. Second fraction 374 can correspond to a $C_{4-}$ stream or (preferably) a $C_{5-}$ stream, depending on the configuration. In aspects, the second fraction 374 is subjected to compression in the treatment system 375. Compression in treatment system 375 can result in generation of a side stream of water 372. The compressed stream then goes through a series of wash steps, such as a methanol wash to remove oxygenates, a water wash to remove methanol, and a caustic wash to remove carbon dioxide. The stream may then be dried to remove water, such as with a molecular sieve drier or by washing with methanol, which itself has preferably been dried to remove water, such as with a molecular sieve drier.

In aspects, the dried by-product mixture 377 is then sent to a fractionation tower 380 primarily to remove dimethyl ether from the light olefins. Dimethyl ether can potentially pose difficulties for a variety of downstream processes, such as processes for olefin recovery and/or polymerization. Additionally, or alternately, if the recovered aliphatic hydrocarbons from methylation are recycled to a (direct) aromatics formation process, the dimethyl ether can potentially cause undesirable reactions under the aromatics formation conditions. The fractionation tower acts to fractionate the dried by-product mixture into an overhead stream 382, containing at least some, and preferably most, of the $C_{3-}$ hydrocarbons, with almost all of the dimethyl ether and $C_{4+}$ hydrocarbons recovered as a liquid bottoms stream 384. For example, ethylene and at least about 80 wt %, preferably at least about 90 wt %, of the propylene, and about 67 wt % of the propane from the fractionation column are recovered in the overhead stream, while nearly 100 wt % of the dimethyl ether (and/or other oxygenates) and nearly 100 wt % of $C_{4+}$ hydrocarbons are removed in the liquid bottoms stream. The overhead vapor stream 382 from the fractionation tower 380, which generally comprises less than about 100 ppm dimethyl ether, preferably 20 ppm or less by weight, more preferably 1 ppm or less by weight is sent to a contaminant removal system.

In aspects, the overhead vapor stream 382 is treated to remove the contaminants from the off-gas stream. In preferred aspects, the overhead vapor stream 382, containing hydrogen, methane, ethane, ethylene, propane, propylene, nitrogen, carbon monoxide, and nitrogen oxides, is fed to an absorber demethanizer 390. An absorber demethanizer is effective at removing the nitrogen, carbon monoxide, and nitrogen oxide contaminants from the off-gas stream without the risks associated with a cryogenic system. The absorber demethanizer operates by contacting the off-gas stream counter-currently with a hydrocarbon absorbent. As the absorbent travels down the column and interacts with the off-gas stream traveling up the column, at least some, and preferably most, of the $C_{2+}$ hydrocarbons in the off-gas stream are absorbed by the absorbent and exit the absorber demethanizer in a bottoms stream 394. The hydrogen, methane, nitrogen, carbon monoxide, and nitrogen oxides, along with a small percentage of the $C_2$ and $C_3$ hydrocarbons, exit the absorber demethanizer as an overhead stream 392, which may be used as fuel. The absorber demethanizer may be equipped with a reboiler to minimize the amount of methane and contaminants in the bottoms stream 394.

The hydrocarbon absorbent may be selected from a $C_2$-$C_6$ hydrocarbon, preferably a $C_3$-$C_5$ hydrocarbon, and more preferably a $C_3$-$C_4$ hydrocarbon or mixture thereof. Examples of suitable hydrocarbon absorbents are ethane, propane, propylene, n-butane, isobutane, n-butylene, isobutylene, 1-butene, cis-butene, trans-butene, butadiene, and pentane. The absorbent is typically free from contaminants that would affect the downstream operations and free from water that could cause hydrate formation in the absorber demethanizer. In a preferred aspect, the absorbent used is a $C_3$ or $C_4$ hydrocarbon or a mixture thereof. For example, the absorbent may be propylene, a $C_4$ hydrocarbon, or a mixture of propylene and $C_4$ hydrocarbons, such as propylene and butenes. In a more preferred embodiment, the absorbent used is a $C_4$ hydrocarbon or a mixture of $C_4$ hydrocarbons, as fewer $C_4$ hydrocarbons are lost to fuel in the absorber demethanizer relative to $C_3$ hydrocarbon absorbents. For example, the absorbent may be n-butane, isobutane, isobutylene, 1-butene, cis-butene, trans-butene, butadiene, or a mixture thereof. The absorbent used may also contain an amount of other components that do not materially affect the characteristics of the absorbent. Thus, a $C_3$ hydrocarbon absorbent may also contain an amount of $C_2$ hydrocarbons, but the amount of $C_2$ hydrocarbons does not affect the characteristics of the $C_3$ hydrocarbon absorbent. Likewise, a $C_4$ hydrocarbon absorbent may also contain an amount of $C_3$ hydrocarbons, but the amount of $C_3$ hydrocarbons does not affect the characteristics of the $C_4$ hydrocarbon absorbent.

It should be appreciated that the optimum operating temperature and pressure for the absorber demethanizer will depend on the hydrocarbon absorbent used, available refrigerant and desired economic recovery. Typically, the higher the operating temperature, the lesser the risk of formation of nitrogen oxide salts and gums.

The bottoms stream 394 containing the absorbent, $C_2$ and $C_3$ hydrocarbons are sent to a separation system 395, typically a fractionation column or columns, where the absorbent is separated for recirculation through the absorber demethanizer 390. The separation system 395 may be selected based upon the absorbent used. For example, the separation system 395 can be a single fractionation column to concentrate the hydrocarbon absorbent for reuse. In aspects where a $C_4$ hydrocarbon or a mixture of $C_4$ hydrocarbons is used as the absorbent, the separation system 395 includes a depropanizer. The bottoms stream 394 from the absorber demethanizer enters the separation system 395, which separates the $C_2$ and $C_3$ hydrocarbons from the $C_4$ hydrocarbon absorbent. The $C_2$ and $C_3$ hydrocarbons exit the separation system 395 as an overhead stream 397 and are sent to further processing in an olefins plant/process to yield valuable light alkanes and olefins. The absorbent leaves the separation system 395 as a bottoms stream 398 for recirculation through the absorber demethanizer 390. Additional absorbent 396, to offset the losses, may be introduced into the separation system 395.

Figure 4:
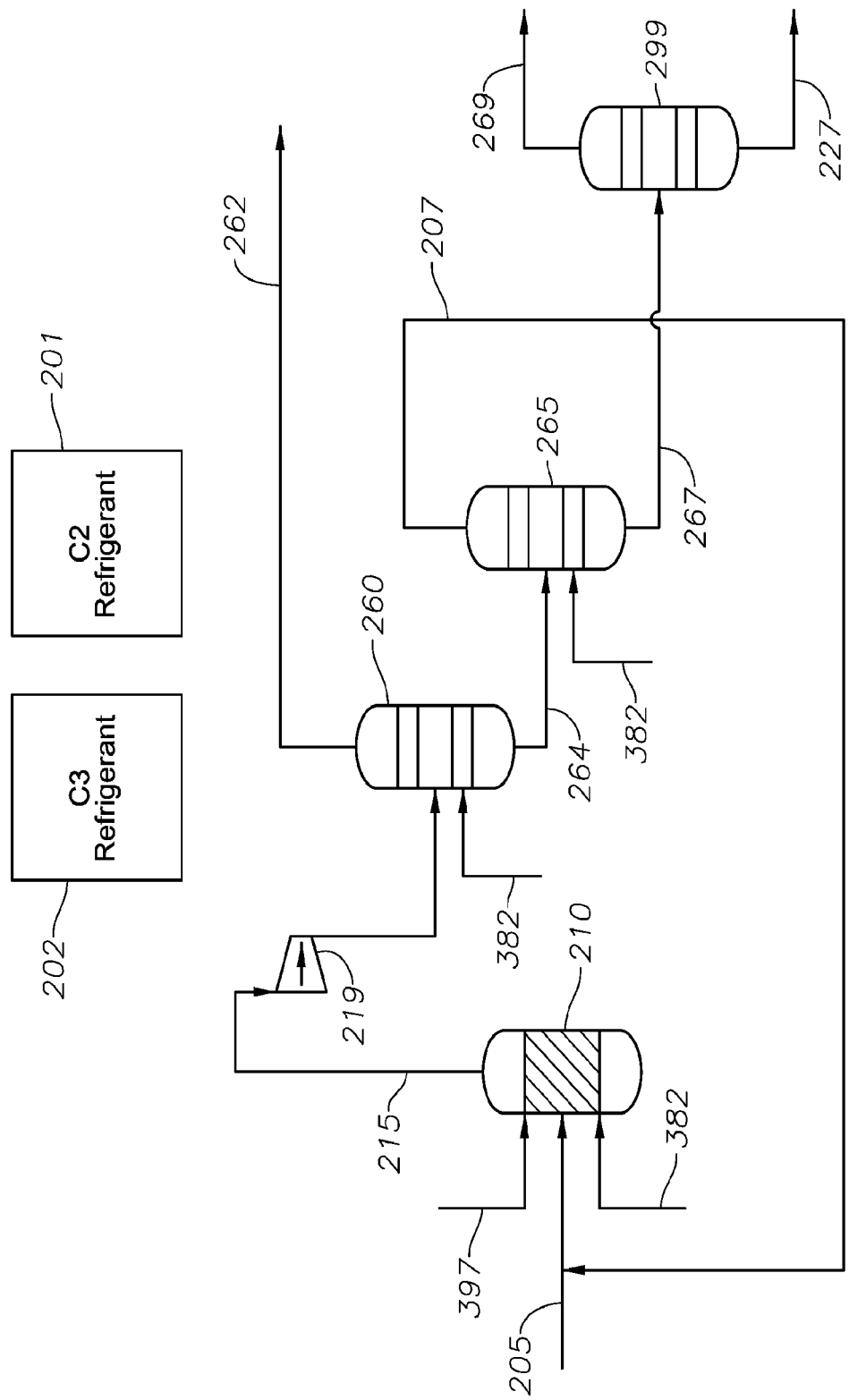
FIG. 4 schematically shows an example of an integrated system for performing separations on effluents from an aromatic formation process and an alkylation process.

FIG. 4 schematically shows various examples of how the separation process flow shown in FIG. 2 can be integrated with the separation process flow shown in FIG. 3. In FIG. 4, the separation scheme from FIG. 2 is shown with additions to indicate locations where output streams from FIG. 3 can be inserted. For example, FIG. 4 includes three distinct options for using alone or in combination at least a portion of overhead vapor stream 382 from FIG. 3 as an input flow for the system in FIG. 2. Overhead vapor stream 382 can be a suitable stream for introduction into the process flow shown in FIG. 2 based on the reduced or minimized content of dimethyl ether in overhead vapor stream 382. Some of the difficulties in integrating the by-product processing of an aromatics formation reactor and the by-product processing of a methylation reactor can be related to the presence of dimethyl ether in the by-products from methylation. The presence of oxygenates such as dimethyl ether in an aromatics formation process can potentially be disruptive for the desired conversion of non-aromatics (such as alkanes) to aromatic compounds. However, any dimethyl ether (or other oxygenates) remaining in the washed and dried by-product mixture 377 from methylation can be separated into liquid bottoms stream 384 in separation stage 380. As a result, overhead vapor stream 382 can be suitable for incorporation into a process train that eventually produces a recycle stream for transfer to an aromatics formation process as part of the feed. As shown in FIG. 4, overhead vapor stream 382 (or a portion thereof) can potentially be used directly as an additional feed stream for aromatic formation process 210. Other options can include introducing overhead vapor stream 382 (or a portion thereof) into the demethanizer 260 and/or the depentanizer 265. Introducing overhead vapor stream 382 in one of these locations can result in the overhead vapor stream 382 undergoing additional separation along with the by-product effluent from the aromatic formation process. After the additional separation, the $C_{2+}$ hydrocarbon portion of vapor stream 382 can be transferred to the aromatic formation process 210 as a recycled portion of the hydrocarbon feed.

In certain aspects, overhead stream 397, which includes $C_2$ and $C_3$ hydrocarbons, is introduced into aromatic formation process 210. Because overhead stream 397 is substantially composed of $C_2$ and $C_3$ hydrocarbons, no additional separation is needed. However, if desired, overhead stream 397 could be introduced into a separation stage, after optional additional compression, such as demethanizer 260 and/or depentanizer 265.

Figure 5:
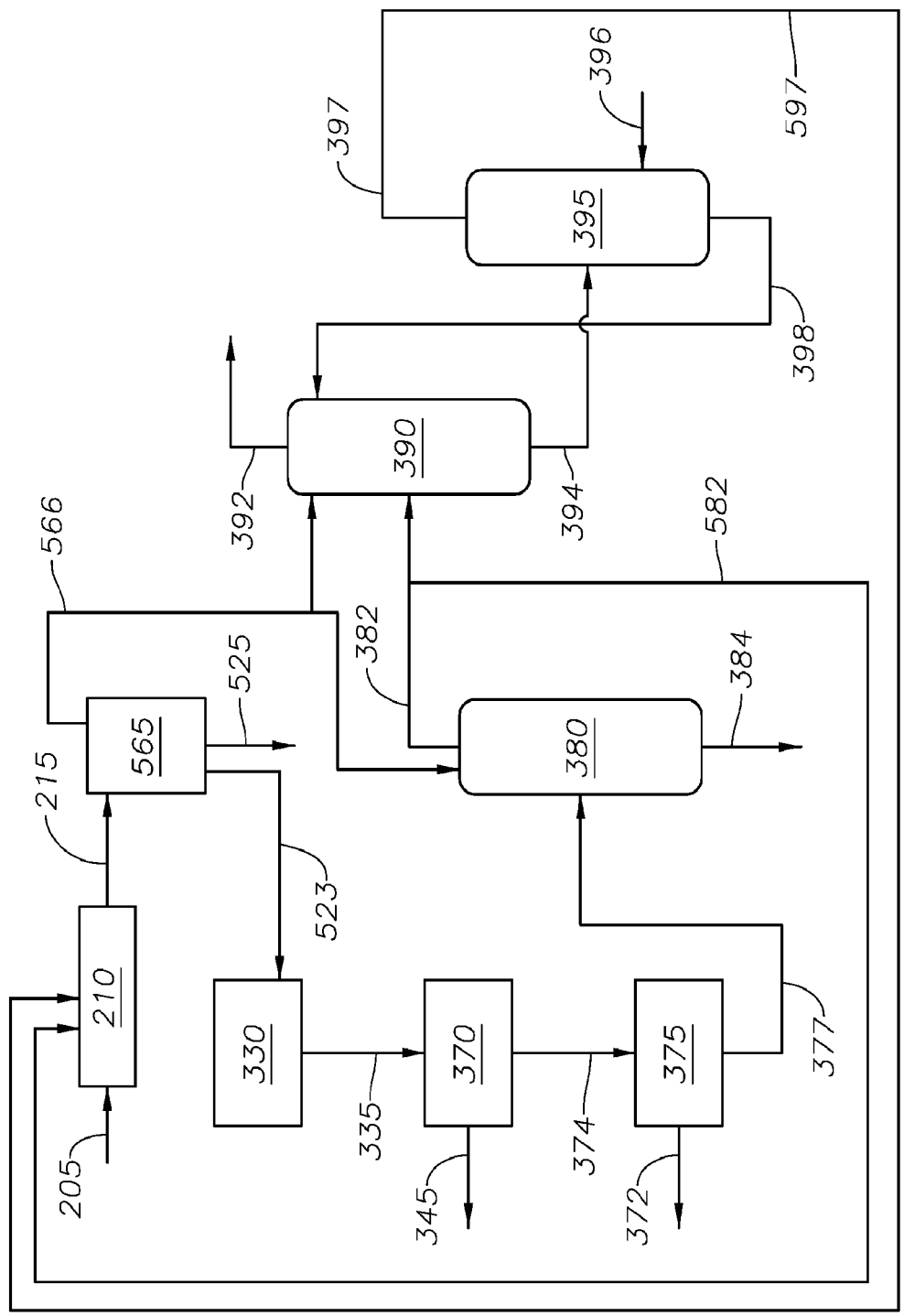
FIG. 5 schematically shows another example of an integrated system for performing separations on effluents from an aromatic formation process and an alkylation process.

FIG. 5 schematically shows another example of integration of processing the by-product or secondary effluent streams from aromatic formation and methylation. In FIG. 5, the aromatic formation effluent 215 from an aromatic formation process 210 is passed into a separation process 565. Separation process 565 can produce a $C_{5-}$ stream 566. This can correspond to, for example, introducing aromatic formation effluent 215 into a depentanation stage, as opposed to initially introducing the aromatic formation effluent into a demethanation stage as shown in FIG. 2. The resulting $C_{5-}$ stream 566 can then be passed into separation stage 380, or alternatively can be passed into absorber demethanizer 390. Depending on the configuration, the overhead stream 382 (or at least a portion 582 thereof) from separation stage 380 can be recycled as an input flow for aromatic formation process 210. Additionally, or alternatively, the $C_2$-$C_3$ stream 397 (or at least a portion 597 thereof) from separation stage 395 can be recycled/transferred as an input flow to aromatic formation process 210. It is noted that $C_2$-$C_3$ stream 397 can include an elevated content of $C_4$ and/or $C_5$ compounds when $C_{5-}$ stream 566 is introduced into absorber demethanizer 390.

Additionally, separation process 565 can optionally include additional stages for separating a $C_8$ aromatics stream 525 and/or a $C_6$-$C_7$ aromatics stream 523 from the aromatic formation effluent. As shown in FIG. 5, the $C_6$-$C_7$ stream 523 can be used as an input flow for methylation process 330.

Thermal Integration—$C_2$ Refrigerant

After forming product streams that contain xylene, such as product streams 125 and/or 145 in FIG. 1, an additional difficulty can be recovering a higher value product such as para-xylene from lower value isomers such as ethylbenzene, ortho-xylene, and/or meta-xylene. One option for separating para-xylene from other $C_8$ isomers is via a crystallization process. Crystallization for xylene separation is well known in the art, and is discussed, for example, in U.S. Pat. No. 7,989,672 and WO95/26946, both of which are incorporated herein by reference with regard to description of separation of para-xylene by crystallization.

One of the difficulties with separation of para-xylene by crystallization is that the yield of para-xylene can be limited based on the coldest crystallization stage that is available. A cooling system using an ethylene refrigerant can often correspond to the coldest practical refrigerant available. Due to the expense of operating a cooling system using an ethylene refrigerant, crystallization can be economically less favorable relative to other methods of xylene separation. However, this additional expense can be mitigated by using a cooling system including a $C_2$ refrigerant (such as ethylene) for multiple purposes within a xylene production system.

As an example, FIG. 2 shows a process flow for processing of the secondary effluent stream from an aromatics formation process. Demethanation stage 260 corresponds to a stage using an ethylene refrigerant in order to perform the demethanation. Instead of sizing the cooling system based only on demethanation stage 260, the cooling system can be sized to accommodate other, additional processes. One additional process can correspond to a xylene crystallizer. A second additional process that can potentially benefit from ethylene refrigerant is separation stage 380 in FIG. 3.

Additional Integration—Styrene Hydrogenation

An additional difficulty with processing $C_8$ aromatic streams derived from methylation of benzene and/or toluene using methanol and/or dimethyl ether can be related to the presence of styrene in the stream. Under the methylation conditions, a portion of styrene (and/or other aromatics having olefinic side chains) can be formed in addition to the desired xylene products. The styrene (and/or other aromatics with olefinic side chains) can be harmful to the xylene separation process if it is allowed to remain in the $C_8$ aromatic stream during xylene separation. One option for removing the aromatics with olefinic side chains can be to at least partially saturate the unsaturated side chains of such aromatics (i.e., at least partially convert styrene to ethylbenzene) in the presence of hydrogen and a catalyst with activity for olefin saturation. Suitable catalysts include those having 0.1 wt. % to 1.5 wt. % Pd supported on a refractory oxide support, such as alumina.

In some aspects, the hydrogen for performing olefin saturation on styrene within a $C_8$ aromatic stream can be obtained from hydrogen generated during an aromatic formation process. As shown in FIG. 2, lower boiling fraction 262 from the demethanation stage 260 can include methane and hydrogen. Conventional separation methods can be used to recover the $H_2$ from lower boiling fraction 262. For example, stream 145 in FIG. 1 can be exposed to a styrene saturation catalyst in the presence of hydrogen recovered from lower boiling fraction 262. Styrene saturation can be performed by any convenient method. U.S. Pat. No. 9,416,072 (incorporated by reference herein) describes a suitable method for exposing a $C_8$ aromatic stream to a styrene saturation catalyst in the presence of hydrogen.

Aromatic Formation Process—General Operation

The aromatics formation process's feed typically comprises one or more $C_1$ to $C_9$ non-aromatic hydrocarbon compounds, e.g., one or more light hydrocarbon (i.e., $C_1$ to $C_5$) compounds, such as one or more paraffinic light hydrocarbon compounds. For example, the feed can comprise ≥1 wt. % based on the weight of the feed of one or more of (i) paraffinic $C_2$ to $C_9$ hydrocarbon, (ii) aliphatic $C_1$ to $C_9$ hydrocarbon, (iii) aliphatic paraffinic $C_1$ to $C_9$ hydrocarbon, (iv) paraffinic light hydrocarbon, (v) aliphatic light hydrocarbon, and (vi) aliphatic paraffinic light hydrocarbon; such as ≥10 wt. %, or ≥25 wt. %, or ≥50 wt. %, or ≥75 wt. %, or ≥90 wt. %, or ≥95 wt. %. Optionally, the feed further comprises diluent. Diluent present in the feed's source (e.g., methane and/or $CO_2$ present in natural gas) and diluent added to the feed are within the scope of the invention. Diluent, when present, is typically included in the feed in an amount ≤60 wt. % based on the weight of the feed, e.g., ≤50 wt. %, such as ≤40 wt. %, or ≤30 wt. %, or ≤20 wt. %, or ≤10 wt. %. A feed constituent is diluent when it is substantially non-reactive under the specified reaction conditions in the presence of the specified dehydrocyclization catalyst, e.g., methane, molecular nitrogen, and inert atomic gasses such as argon. Organic and inorganic diluents are within the scope of the invention.

The feed's non-aromatic $C_1$ to $C_9$ hydrocarbon can include aliphatic hydrocarbon, e.g., alkane. Representative alkane-containing feeds include those comprising at least 20 mole % of one or more $C_1$-$C_9$ alkane relative to the total number of moles in the feed, or at least 35 mole %, or at least 50 mole %, or at least 60 mole %, or at least 70 mole %, or at least 80 mole %. Additionally, or alternately, the alkane-containing feedstock can initially contain at least 50 mole % of one or more $C_1$-$C_9$ alkane relative to the total number of moles of hydrocarbon in the feed, or at least 60 mole %, or at least 70 mole %, or at least 80 mole %.

The feed can include methane, e.g., ≥1 wt. % methane, such as ≥10 wt. %, or ≥20 wt. %, or ≥60 wt. %. When methane is substantially non-reactive under the specified aromatics formation reaction, the methane is considered diluent. Alternatively, or in addition, the feed can comprise ethane, e.g., ≥1 wt. % ethane, based on the weight of the feed, such as ≥5 wt. %, or ≥10 wt. %, or in the range of from 10 wt. % to 40 wt. %. Suitable feeds include those containing a major amount of ethane, e.g., ≥50 wt. % ethane, such as ≥75 wt. %, or ≥90 wt. %, or ≥95 wt. %. Alternatively, or in addition to the methane and/or ethane, the feed can contain $C_3$ and/or $C_4$ hydrocarbon, e.g., (i) ≥20 wt. % propane, such as ≥40 wt. %, or ≥60 wt. %, and/or (ii) ≥20 wt. % butanes, such as ≥40 wt. %, or ≥60 wt. %. In some aspects, the feed can contain a reduced amount of $C_{5+}$ hydrocarbon, e.g., ≤20 wt. %, such as ≤10 wt. % or ≤01 wt. %. In such aspects, the feed can contain ≤10 wt. % of $C_{6+}$ saturated hydrocarbon, e.g., ≤5 wt. %.

Optionally, the feed comprises molecular hydrogen, e.g., ≥1 wt. % molecular hydrogen based on the weight of the feed, such as ≥5 wt. %. Optionally, the feed contains unsaturated $C_{2+}$ hydrocarbon, such as $C_2$-$C_5$ unsaturated hydrocarbon. When present, the amount of $C_{2+}$ unsaturated hydrocarbon (e.g., $C_2$-$C_5$ unsaturated hydrocarbon) is typically ≤20 wt. %, e.g., ≤10 wt. %, such as ≤1 wt. %, or ≤0.1 wt. %, or in the range of from 0.1 wt. % to 10 wt. %. Typically, the feed is substantially-free of aromatic hydrocarbon, where substantially-free in this context means an aromatic hydrocarbon concentration that is ≤1 wt. % based on the weight of the feed, such as ≤0.1 wt. %, or ≤0.01 wt. %, or ≤0.001 wt. %. Typically, the feed comprises a total of ≤10 wt. % of impurities such as CO, $CO_2$, $H_2S$, and total mercaptan, e.g., ≤1 wt. % or ≤0.1 wt. %. One representative feed comprises 1 wt. % to 40 wt. % methane; ≥10 wt. % ethane, such as in the range of from 10 wt. % to 40 wt. %; 20 wt. % to 50 wt. % propane; and 20 wt. % to 50 wt. % butanes.

The feed's light hydrocarbon can be obtained from one or more sources of hydrocarbon, e.g., from natural hydrocarbon sources such as those associated with producing petroleum, or from one or more synthetic hydrocarbons sources such as catalytic and non-catalytic reactions. Examples of such reactions include catalytic cracking, catalytic reforming, coking, steam cracking, etc. Synthetic hydrocarbon sources include those in which hydrocarbon within a geological formation has been purposefully subjected to one or more chemical transformations. The feed can include components recycled from the process, e.g., from one or more locations downstream of the aromatics formation.

In certain aspects, the source of light hydrocarbon includes natural gas, e.g., raw natural gas ("raw gas"). Natural gas is (i) a mixture comprising hydrocarbon, (ii) primarily in the vapor phase at a temperature of 15° C. and a pressure of 1.013 bar (absolute), and (iii) withdrawn from a geologic formation. Natural gas can be obtained, e.g., from one or more of petroleum deposits, coal deposits, and shale deposits. The natural gas can be one that is obtained by conventional production methods but the invention is not limited thereto. Raw natural gas is a natural gas obtained from a geologic formation without intervening processing, except for (i) treatments to remove impurities such as water and/or any other liquids, mercaptans, hydrogen sulfide, carbon dioxide; and (ii) vapor-liquid separation, e.g., for adjusting the relative amounts of hydrocarbon compounds (particularly the relative amounts of $C_{4+}$ hydrocarbon compounds) in the natural gas; but not including (iii) fractionation with reflux. Conventional methods can be used for removing impurities and/or adjusting the relative amount of hydrocarbon compounds present in the feed, but the invention is not limited thereto. For example, certain components in the natural gas can be liquefied by exposing the natural gas to a temperature in the range of −57° C. to 15° C., e.g., −46° C. to 5° C., such as −35° C. to −5° C. At least a portion of the liquid phase can be separated in one or more vapor-liquid separators, e.g., one or more flash drums. One suitable raw natural gas comprises 3 mole % to 70 mole % methane, 10 mole % to 50 mole % ethane, 10 mole % to 40 mole % propane, 5 mole % to 40 mole % butanes and 1 mole % to 10 mole % of total $C_5$ to $C_9$ hydrocarbon. In certain aspects, ≥50 wt. % of the feed comprises natural gas, such as raw natural gas, e.g., ≥75 wt. %, or ≥90 wt. %, or ≥95 wt. %.

Any form of raw gas can be used as a source material, although the raw gas is typically one or more of (i) gas obtained from a natural gas well ("Gas Well", Non-associated", or "Dry" gas), (ii) natural gas obtained from a condensate well ("Condensate Well Gas"), and (iii) casing head gas ("Wet" or "Associated" gas). Table 1 includes typical raw gas compositional ranges (mole %) and, parenthetically, typical average composition (mole %) of certain raw gasses.

TABLE 1

| Component | Associated Gas | Dry Gas | Condensate Well Gas |
|---|---|---|---|
| $CO_2$ | 0-50 (0.63) | 0-25 (0) | 0-25 (0) |
| $N_2$ | 0-50 (3.73) | 0-25 (1.25) | 0-25 (0.53) |
| $H_2S$ | 0-5 (0.57) | 0-5 (0) | 0-5 (0) |

TABLE 1-continued

| Component | Associated Gas | Dry Gas | Condensate Well Gas |
|---|---|---|---|
| $CH_4$ | 0-80 (64.48) | 0-97 (91.01) | 0-98 (94.87) |
| $C_2H_6$ | 5-20 (11.98) | 2-10 (4.88) | 1-5 (2.89) |
| $C_3H_8$ | 2-10 (8.75) | 0.5-5 (1.69) | 0.1-5 (0.92) |
| i-butane | 0.1-5 (0.93) | 0.05-1 (0.14) | 0.1-5 (0.31) |
| n-butane | 1-5 (2.91) | 0.05-2 (0.52) | 0.05-2 (0.22) |
| i-pentane | 0.05-2 (0.54) | 0.01-1 (0.09) | 0.01-1 (0.09) |

In certain aspects, the feed comprises ≥75 wt. % Associated Gas, based on the weight of the feed, e.g., ≥90 wt. % or ≥95 wt. %.

The invention is therefore particularly advantageous in remote or under-developed locations, where (i) the lack of cryogenic methane separation facilities limits the utility of conventional natural gas aromatization processes, (ii) the lack of a pipeline or natural gas production infrastructure, may result in significant quantities of light hydrocarbon being flared or burned as fuel, and (iii) Associated Gas remains stranded at a remote location for lack of pipeline facilities or a failure to meet one or more specifications of an available pipeline. Small scale plants using the present process would allow effective recovery of these light hydrocarbon resources as liquid hydrocarbons.

It is within the scope of the invention for one or more of the specified feeds to be particularly advantageous in connection with a particular aromatics formation process. Consequently, the choice of feed may depend at least in part on the aromatics formation process utilized in a particular aspect. For example, certain aspects utilize a feed comprising at least 10 mole % of particular alkane relative to the total moles of $C_1$-$C_9$ alkane in the feed, or at least 20 mole %, or at least 30 mole %, or at least 40 mole %, or at least 50 mole %, or at least 60 mole %, or at least 70 mole %, and/or up to about 100 mole % or less, or 90 mole % or less, or 80 mole % or less, or 70 mole % or less, or 60 mole % or less, or 50 mole % or less, or 40 mole % or less, or 30 mole % or less. The particular alkane can be one or more of methane, ethane, propane, or butanes, e.g., methane and ethane. Additionally, or alternately, the feed can contain 50 mole % or less of $C_5$-$C_9$ alkane relative to the total moles of $C_1$-$C_9$ alkane in the feed, or 40 mole % or less, or 30 mole % or less, or 20 mole % or less, or 10 mole % or less, or the feed can be substantially free of $C_5$-$C_9$ alkane, such as 5 mole % or less, or 1 mole % or less.

As described in more detail below, the specific conditions for an aromatic formation process will depend on the nature of the process used for aromatic formation. In some aspects, any convenient aromatic formation process can be suitable. In other aspects, a suitable aromatic formation process can have one or more characteristics related to conversion of feed components; relative conversion of specific components within a feed; selectivity (i.e., yield) for one or more types of $C_8$ aromatic hydrocarbon; and/or relative selectivities for aromatic hydrocarbon.

The amount of conversion of one or more specified feed components can be used to characterize an aromatic formation process. For example, an aromatic formation process can be characterized based on conversion of $C_1$-$C_9$ alkane in a feed. The following feed conversion amounts represent conversion in a single pass. Certain aromatics formation processes convert at least 20 wt. % of particular alkane in the feed, or at least 30 wt. %, or at least 40 wt. %, or at least 50 wt. %, or at least 60 wt. %, or at least 70 wt. %, and/or up to 100 wt. % or less, or 90 wt. % or less, or 80 wt. % or less, or 70 wt. % or less, or 60 wt. % or less. Alternatively, or in addition, an aromatics formation process can convert a relative amount of particular alkane. For example, in certain aromatics formation processes at least 1 wt. % of the total alkane converted in the aromatic formation process are particular alkane, or at least 5 wt. %, or at least 10 wt. %, or at least 20 wt. %, or at least 30 wt. %, or at least 40 wt. %, or at least 50 wt. %, and/or up to 100 wt. % or less, or 90 wt. % or less, or 80 wt. % or less, or 70 wt. % or less, or 60 wt. % or less. The particular alkane can be, e.g., (i) one or more $C_1$ to $C_9$ alkane compounds, (ii) one or more $C_1$ to $C_4$ alkane compounds, (iii) one or more $C_{5+}$ alkane compounds, and (iv) methane and/or ethane. It is noted that each of the above lower bounds for an amount of alkane conversion is explicitly contemplated with each of the above upper bounds.

The selectivity for production of benzene, $C_7$ aromatic hydrocarbon, and/or $C_8$ aromatic hydrocarbon is yet another way to characterize an aromatic formation process, e.g., the selectivity for production of benzene, $C_7$ aromatic hydrocarbon, and/or $C_8$ aromatic hydrocarbon in the aromatics formation process's effluent. For example, the amount of particular aromatic hydrocarbon in the process effluent can be 40 wt. % of the total aromatic hydrocarbon in the effluent, or at least 50 wt. %, or at least 60 wt. %, or at least 70 wt. %, or 20 wt. % or less, or 10 wt. % or less, or 5 wt. % or less of the total aromatic hydrocarbon in the effluent. The particular aromatic hydrocarbon can be one or more $C_6$ to $C_8$ aromatic hydrocarbon compounds, e.g., (i) $C_8$ aromatic hydrocarbon and/or (ii) $C_6$-$C_7$ aromatic hydrocarbon. More particularly, an aromatic formation process can be characterized based on the selectivity for production of one or more particular $C_8$ aromatic hydrocarbon relative to the total amount of $C_8$ aromatic hydrocarbon in the process effluent. For example, the amount of ethylbenzene in the process effluent can be 30 wt. % or less relative to the total $C_8$ aromatic hydrocarbon in the effluent, or 25 wt. % or less, or 20 wt. % or less, or 15 wt. % or less, or 10 wt. % or less. Additionally, or alternately, the amount of ethylbenzene in the effluent can be 25 wt. % or less relative to the total $C_6$-$C_8$ aromatic hydrocarbon in the effluent, or 20 wt. % or less, or 15 wt. % or less, or 10 wt. % or less. In aspects where para-xylene is separated from other $C_8$ aromatic hydrocarbon, a reduced or minimized ethylbenzene concentration can allow for use of a liquid isomerization process as part of a para-xylene recovery loop and/or can reduce or lessen the amount of purge from the liquid isomerization process.

Yet another way to characterize an aromatic formation process is based on the selectivity for production of $C_7$ aromatic hydrocarbon relative to the amount of benzene produced. In certain aspects, the molar ratio of $C_7$ aromatic hydrocarbon (toluene) to the amount of $C_6$ aromatics (benzene) can be at least 1.0, or at least 1.4, or at least 1.5, or at least 1.8, or at least 2.0, or at least 2.5. Typically, benzene is a higher value product, and therefore performing an aromatic formation process to enhance toluene yield is unconventional. In other aspects, the molar ratio of $C_7$ aromatic hydrocarbon (toluene) to benzene can be 1.0 or less, or 0.9 or less, or 0.8 or less, or 0.7 or less, or 0.6 or less.

Factors such as (i) relative value of toluene to benzene and/or (ii) the relative cost of the inputs to the aromatic formations process and the methylation process can be used in selecting a particular molar ratio. For example, as the relative value of toluene increases, the aromatic formation conditions can be altered to generate higher ratios of toluene to benzene. Another option can be to select an increased molar ratio of $C_7$ aromatic hydrocarbon to $C_6$ aromatic hydrocarbon to lessen the formation of olefin and/or other side products during methylation. Converting benzene to toluene during methylation typically uses reaction conditions with increased severity relative to conversion of toluene to xylene. This can lead to additional formation of side products during methylation, potentially resulting in increased recycle of $C_6$-$C_7$ components.

In aspects where at least a portion of the methane in the feed is converted to methanol, controlling the relative amounts of toluene and benzene can provide further benefits. Depending on the relative cost of methane and the relative cost of the methanol production step within the aromatic formation process, the aromatic formation conditions can be selected to provide a net improved yield of xylene relative to the amount of carbon in the feed. For example, aromatic formation conditions that lower production of xylene can also tend to reduce or minimize ethylbenzene formation. Subsequent methylation of benzene or toluene to form $C_8$ aromatic hydrocarbon also tends to lead to reduced or minimized concentrations of ethylbenzene. If the cost of producing methanol is low relative to the other feed components for aromatic formation, increasing the amount of xylene formed by methylation of toluene and/or benzene can be a beneficial way to add carbon for formation of $C_8$ aromatic hydrocarbon while reducing or minimizing the ethylbenzene concentration.

Examples of Aromatic Formation Processes

Examples of suitable conversion processes for forming aromatic hydrocarbon from non-aromatic hydrocarbon include oxidative coupling methods; co-conversion of methane with co-reactants; reforming of alkane to form syngas, which can then be converted directly to aromatic hydrocarbon or converted via formation of an intermediate such as a methanol or another oxygenate; dehydroaromatization of $C_{3+}$ alkane; conversion of ethane or larger alkane to aromatic hydrocarbon in presence of metal activated ZSM-5 or ZSM-11; conversion of methane on Mo ZSM-5 or any molybdenum carbide type catalyst; or others. In some aspects, it can be preferable to use a direct aromatic formation process that involves conversion of $C_{2+}$ hydrocarbons to aromatics, such as $C_2$-$C_5$ hydrocarbons. Optionally, such a direct aromatic formation process can correspond to a process where 2.0 wt. % or less of methane present in a feed is converted under the aromatic formation conditions, or 1.0 wt. % or less, or substantially no methane conversion occurs (i.e., less than 0.1 wt. % methane conversion). Optionally, such a direct aromatic formation process can be performed on a feed having a methane content of 5.0 wt. % or less, for example 0.1 wt. % to 5.0 wt. %, or 0.01 wt. % to 2.0 wt. %, or 0.1 wt. % to 2.0 wt. %, or 2.0 wt. % to 5.0 wt. %. Optionally, such a direct aromatic formation process can be performed on a feed that includes less than 0.3 moles of methane per mole of $C_1$-$C_9$ alkane in the feed, or less than 0.2 moles, or less than 0.1 moles.

Indirect Processes

One indirect process includes converting methane (and/or other alkane) to aromatic hydrocarbon. For example, alkane can be reformed to form CO, $CO_2$, $H_2O$, and $H_2$ (i.e., syngas), and the syngas can then be used to synthesize a variety of larger compounds. The molar ratio of $H_2$ to CO generated during reforming can depend on the type of reforming, such as higher ratios of $H_2$ to CO for steam reforming. The syngas can be produced by any convenient method, including conventional methods such as the partial oxidation of methane and/or the steam reforming of methane. Suitable methods include those described in U.S. Patent Application Publication Nos. 2007/0259972, 2008/0033218, and 2005/0107481, each of which is incorporated by reference herein in its entirety. The resulting syngas can then, for example, be converted to $C_{2+}$ alkane using a Fischer-Tropsch type reaction. Such $C_{2+}$ compounds can then be converted to aromatic hydrocarbon, such as using one or more of the processes identified herein.

In other indirect processes, the syngas is converted to methanol and/or dimethyl ether (DME). The methanol and/or DME are then converted to aromatic hydrocarbon in an aromatics conversion process. For example, the conversion of syngas to methanol (or other alcohols) can be carried out at very high selectivity using a mixture of copper, zinc oxide, and alumina at a temperature of 200° C. to 400° C. and pressures of 50-500 atm. In addition to $Cu/ZnO/Al_2O_3$, other catalyst systems suitable for methanol synthesis include $Zn/VCr_2O_3$, $Cu/ZnO$, $Cu/ZnO/Cr_2O_3$, $Cu/ThO_2$, $CoS_x$, $MoS_x$, $Co-MoS_x$, $Ni-S_x$, $Ni-MoS_x$, and $Ni-Co-MoS_x$.

Suitable processes for converting methanol and/or DME to aromatic hydrocarbon include the MTG (methanol to gasoline) process. The MTG process is disclosed in the patent art, including, for example, U.S. Pat. Nos. 3,894,103; 3,894,104; 3,894,107; 4,035,430; and 4,058,576. U.S. Pat. No. 3,894,102 discloses the conversion of synthesis gas to gasoline. MTG processes provide a simple means of converting syngas to high-quality gasoline. The ZSM-5 catalyst used is highly selective to gasoline under methanol conversion conditions, and is not known to produce distillate range fuels, because the $C_{10+}$ olefin precursors of the desired distillate are rapidly converted via hydrogen transfer to heavy polymethylaromatics and $C_4$ to $C_8$ isoparaffins under methanol conversion conditions.

More generally, conversion of methanol (and/or dimethyl ether) to aromatic hydrocarbon can be performed using as a catalyst a composition of matter comprising a molecular sieve and a Group 8-14 element, or a molecular sieve and a combination of metals from the same group of the Periodic Table. The composition of matter can optionally further comprise phosphorus and/or lanthanum and/or other elements from Group 1-2 and/or Group 13-16 of the Periodic Table that provide structural stabilization. Many examples of conversion of methanol and/or olefin to aromatic hydrocarbon are conventionally known, such as the processes described in U.S. Patent Application Publication 2015/0175499, the entirety of which is incorporated herein by reference.

An example of a suitable catalyst for conversion of $C_{2+}$ or $C_{3+}$ alkane can be a medium pore molecular sieve, such as ZSM-5, that includes both a) Zn as a supported metal or in the catalyst framework and b) phosphorus as a supported metal. The catalyst can correspond to a bound or self-bound catalyst. The ZSM-5, ZSM-11, or other medium pore zeolite can include about 0.1 wt. % to about 5 wt. % of Zn and about 0.1 wt. % to about 5 wt. % of P. A feed containing $C_1$-$C_9$ alkane can be exposed to the catalyst for conversion of alkane to aromatic hydrocarbon under conditions similar to those noted above for dehydroaromatization. It is noted that for processes including conversion of $C_{2+}$ alkane and/or conversion of oxygenates, both benzene and toluene can typically be produced in substantial quantities. In such aspects, the relative amounts of benzene and toluene produced can be dependent on the reaction conditions, so that the relative amounts of benzene and toluene produced can be controlled.

Direct Processes

Certain suitable direct processes for aromatics formation include methane dehydrocyclization. Although methane is abundant, the relative inertness of methane has conventionally limited its utility in direct conversion processes for producing higher-value hydrocarbon. This difficulty can be at least partially overcome using methods described in U.S. Pat. No. 8,378,162, the entirety of which is incorporated herein by reference. The disclosed methods include converting methane (and optionally other alkane compounds) by a non-oxidative aromatization process at elevated temperatures, such as greater than about 700° C. or greater than about 800° C. Such processes typically produce an aromatic product comprising primarily benzene, with little or no production of $C_{7+}$ aromatic hydrocarbon, such as para-xylene. For example, such processes typically exhibit (i) a benzene to toluene molar ratio of at least about 8:1, or at least about 10:1, or at least about 15:1, or at least about 20:1; and/or (ii) benzene to ethylbenzene molar ratio of at least about 10:1, or at least about 15:1, or at least about 20:1, or at least about 30:1. Optionally, a portion of a natural gas feed (or other methane-containing feed) used for direct conversion of methane to aromatic hydrocarbon can also be used for methanol production, so that a single feed source can provide methanol for a subsequent alkylation stage to form para-xylene from the benzene generated by methane conversion. Other suitable direct processes for methane dehydrocyclization utilize a co-reactant. For example, U.S. Pat. No. 5,936,135 discloses reacting methane at a temperature in the range of 300° C. to 600° C. with (i) a $C_{2-10}$ olefin and/or (ii) a $C_{2-10}$ paraffin in the presence of a bifunctional pentasil zeolite catalyst, having strong dehydrogenation and acid sites, to produce aromatic hydrocarbon. The preferred mole ratio of olefin and/or higher paraffin to methane and/or ethane in the feed ranges from about 0.2 to about 2.0. The use of organic oxygenate as a co-reactant is disclosed in U.S. Pat. No. 7,022,888. The organic is represented by a general formula: $C_nH_{2n+1}OC_mH_{2m+1}$, wherein C, H and O are carbon, hydrogen and oxygen, respectively; n is an integer having a value between 1 and 4; and m is an integer having a value between zero and 4. The methane and oxygenate are converted to $C_{2+}$ hydrocarbon, particularly to gasoline range $C_6$-$C_{10}$ hydrocarbon and hydrogen, using a bifunctional pentasil zeolite catalyst, having strong acid and dehydrogenation functions, at a temperature below 700° C.

Alternatively or in addition to methane aromatization, certain suitable direct processes for aromatics formation include aromatization of $C_{2+}$ hydrocarbon, e.g., those carried out under relatively mild conditions compared to those needed for methane aromatization. For example, U.S. Pat. No. 4,788,364 (incorporated herein by reference with regard to the description of a catalyst and general reaction conditions for aromatic formation), describes a method for conversion of $C_2$-$C_{10}$ alkane to aromatic hydrocarbon in the presence of a conversion catalyst and optionally further in the presence of an olefin co-feed. The catalyst can include a molecular sieve such as ZSM-5, ZSM-11, ZSM-12, ZSM-22, and/or ZSM-35. The catalyst can further include a catalytic metal such as P, Ga, Sn, Re, Zn, Pt, and/or Cu, which can be incorporated by ion exchange, impregnation by incipient wetness, or any other convenient method. The reaction can occur in two zones, with dehydrogenation to form olefins and aromatic hydrocarbon in a first zone, and oligomerization and further dehydrocyclization occurring in a second zone. The reaction is performed at a pressure of 50 to 2000 kPa, with a temperature in the first zone of 537° C. to 895° C. and a temperature in the second zone of 215° C. to 535° C. A riser reactor can be a convenient configuration for providing the desired reaction conditions for the two zones while using a catalyst compatible for catalyzing the reaction in both zones. Converting $C_{3+}$ non-aromatic hydrocarbon, e.g., $C_{3+}$ alkane, to aromatic hydrocarbon can be accomplished under relatively less severe conditions than conversion of methane or $C_2$ hydrocarbon, such as by using a dehydroaromatization process. An example of a dehydroaromatization process is described in U.S. Pat. No. 5,043,502. Briefly, an alkane-containing feed can be exposed to a catalyst at a temperature of about 350° C. to about 650° C., or about 400° C. to about 550° C., a pressure of about 1 to about 20 atmospheres or about 2 to about 10 atmospheres, and a liquid hourly space velocity (LHSV) of about 0.2 to about 5.0 $hr^{-1}$ or about 0.5 to about 2.0 $hr^{-1}$. The catalyst can correspond to a medium pore zeolite, such as ZSM-5, that also includes a gallium component. At higher temperature conditions, the process can also allow for some ethane conversion. More generally, $C_{2+}$ alkane can be converted to aromatic compounds based on exposure of an alkane containing feed to a medium pore molecular sieve, such as ZSM-5 or ZSM-11. The medium pore molecular sieve can be one that a supported catalytic metal and/or incorporates an additional metal component such as Ga and/or Zn.

The invention will now be described with respect to a particular aromatics formation process which includes the dehydrocyclization of $C_{2+}$ non-aromatic hydrocarbon, e.g., $C_2$-$C_9$ non-aromatic hydrocarbon, such as $C_2$-$C_9$ paraffinic hydrocarbon, or raw gas. The invention is not limited to these aspects, and this description is not meant to foreclose the use of other aromatics formation processes within the broader scope of the invention. In this form of dehydrocyclization, a feed, e.g., one comprising raw gas, is reacted in the presence of a catalytically effective amount of at least one dehydrocyclization catalyst located in at least one reaction zone operating under catalytic dehydrocyclization conditions. The reaction converts at least a portion of the feed's $C_2$-$C_9$ non-aromatic hydrocarbon to aromatic hydrocarbon and molecular hydrogen. Typically, the dehydrocyclization catalyst comprises ≥10 wt. % of a molecular sieve component and ≥0.005 wt. % of a dehydrogenation component. When the molecular sieve component and dehydrogenation component together comprise less than 100 wt. % of the catalyst, ≥90 wt. % of the remainder of the catalyst can comprise a matrix component, such as ≥99 wt. % of the remainder. The catalyst typically comprises the molecular sieve component in an amount ≥20 wt. %, based on the weight of the catalyst, e.g., ≥25 wt. %, such as in the range of from 30 wt. % to 99.9 wt. %. In certain aspects, the molecular sieve component comprises aluminosilicate, e.g., ≥90 wt. % of at least one aluminosilicate. The aluminosilicate can be an un-substituted aluminosilicate, a substituted aluminosilicate, or a combination thereof.

The molecular sieve component typically comprises ≥90 wt. % of one or more of the specified molecular sieves, e.g., ≥95 wt. %. In certain aspects, the molecular sieve component comprises at least one zeolite molecular sieve, e.g., ≥90 wt. % zeolite, such as ≥95 wt. %, based on the weight of the molecular sieve component. Although the molecular sieve component can consist essentially of or even consist of zeolite, in alternative aspects the zeolite(s) is present in the molecular sieve component in combination with other (e.g., non-zeolitic) molecular sieve. The zeolite can be one that is in hydrogen form, e.g., one that has been synthesized in the alkali metal form, but is then converted from the alkali to the hydrogen form. Typically, the zeolite is one having a medium pore size and a Constraint Index of 2-12 (as defined in U.S. Pat. No. 4,016,218). Examples of suitable zeolites include ZSM-5, ZSM-11, ZSM-12, ZSM-22, ZSM-23, ZSM-35, ZSM-48, including any mixtures and intermediates thereof, such as ZSM-5/ZSM-11 admixture. Optionally, the zeolite is one comprising at least one set of pores of substantially uniform size extending through the molecular sieve, wherein geometric mean of the cross-sectional dimensions of each of the sets of pores is ≥5 Å, or ≥5.3 Å, e.g., ≥5.4 Å, such as ≥5.5 Å, or in the range of 5 Å to 7 Å, or 5.4 Å to 7 Å. ZSM-5 and/or ZSM-12 are suitable, particularly H-ZSM-5. For example, the molecular sieve component can comprise ≥90 wt. % of (A) ZSM-5 and/or (B) ZSM-12, based on the weight of the molecular sieve component, e.g., ≥95 wt. % of H-ZSM-5. In certain aspects, the molecular sieve has a relatively small crystal size, e.g., small crystal ZSM-5, meaning ZSM-5 having a crystal size ≤0.05 μm, such as in the range of 0.02 μm to 0.05 μm. Small crystal ZSM-5 and the method for determining molecular sieve crystal size are disclosed in U.S. Pat. No. 6,670,517, which is incorporated by reference herein in its entirety.

In other aspects, the molecular sieve component comprises at least one molecular sieve of the MCM-22 family, e.g., MCM-22 alone or in combination with other molecular sieve, such as one or more of the specified zeolites. As used herein, the term "molecular sieve of the MCM-22 family" (or "material of the MCM-22 family" or "MCM-22 family material" or "MCM-22 family zeolite") includes one or more of: a) molecular sieves made from a common first degree crystalline building block unit cell, which unit cell has the MWW framework topology. (A unit cell is a spatial arrangement of atoms which if tiled in three-dimensional space describes the crystal structure. Such crystal structures are discussed in the "Atlas of Zeolite Framework Types", Fifth edition, 2001, the entire content of which is incorporated as reference); b) molecular sieves made from a common second degree building block, being a 2-dimensional tiling of such MWW framework topology unit cells, forming a monolayer of one unit cell thickness, preferably one c-unit cell thickness; c) molecular sieves made from common second degree building blocks, being layers of one or more than one unit cell thickness, wherein the layer of more than one unit cell thickness is made from stacking, packing, or binding at least two monolayers of one unit cell thickness. The stacking of such second degree building blocks can be in a regular fashion, an irregular fashion, a random fashion, or any combination thereof; and d) molecular sieves made by any regular or random 2-dimensional or 3-dimensional combination of unit cells having the MWW framework topology.

The MCM-22 family includes those molecular sieves having an X-ray diffraction pattern including d-spacing maxima at 12.4±0.25, 6.9±0.15, 3.57±0.07, and 3.42±0.07 Angstrom. The X-ray diffraction data used to characterize the material are obtained by standard techniques using the K-alpha doublet of copper as incident radiation and a diffractometer equipped with a scintillation counter and associated computer as the collection system.

Materials of the MCM-22 family include MCM-22 (described in U.S. Pat. No. 4,954,325), PSH-3 (described in U.S. Pat. No. 4,439,409), SSZ-25 (described in U.S. Pat. No. 4,826,667), ERB-1 (described in European Patent No. 0293032), ITQ-1 (described in U.S. Pat. No. 6,077,498), ITQ-2 (described in International Patent Publication No. WO 97/17290), MCM-36 (described in U.S. Pat. No. 5,250,277), MCM-49 (described in U.S. Pat. No. 5,236,575), MCM-56 (described in U.S. Pat. No. 5,362,697), and mixtures thereof. Related zeolite UZM-8 is also suitable for use as the molecular sieve component.

When the molecular sieve component comprises at least one aluminosilicate, e.g., at least one zeolite, the aluminosilicate's silica:alumina ratio (substantially the same as the aluminosilicate's Si:Al$_2$ atomic ratio) is typically ≥2, e.g., in the range of from 5 to 100. The silica:alumina ratio is meant to represent the Si:Al$_2$ atomic ratio in the rigid anionic framework of the crystalline aluminosilicate. In other words, aluminum in (i) any matrix or binder or (ii) in cationic or other form within the crystalline aluminosilicate's channels is excluded from the silica:alumina ratio. Alternatively, or in addition, the catalyst can be made more resistant to deactivation (and increase aromatic hydrocarbon yield) by including phosphorous with the molecular sieve component. Conventional methods can be utilized for adding phosphorous, but the invention is not limited thereto. When used, the amount of phosphorous is typically ≥1 wt. % based on the weight of the molecular sieve component. For example, when the molecular sieve component comprises aluminosilicate, the phosphorous:aluminum atomic ratio can be in the range of from 0.01 to 1. Zeolite having a higher silica:alumina ratio can be utilized when a lower catalyst acidity is desired, e.g., in the range of from 44 to 100, such as from 50 to 80, or 55 to 75.

In addition to the molecular sieve component, the catalyst comprises ≥0.005 wt. %, based on the weight of the catalyst, of a dehydrogenation component, e.g., at least one dehydrogenation metal. The dehydrogenation component can comprise one or more neutral metals selected from Groups 3 to 13 of the Periodic Table of the Elements, such as one or more of Ga, In, Zn, Cu, Re, Mo, W, La, Fe, Ag, Pt, and Pd, and/or one or more oxides, sulfides and/or carbides of these metals. For example, the dehydrogenation component can be Ga, Zn, or a combination thereof, optionally supported on a catalyst comprising ZSM-5 as the molecular sieve component. Typically, the catalyst comprises ≥0.01 wt. % of the dehydrogenation component, based on the weight of the catalyst. Those skilled in the art will appreciate that when the dehydrogenation component comprises one or more metals of greater catalytic dehydrogenation activity, e.g., Pt, and/or Pd, a lesser amount of dehydrogenation component is needed, e.g., in the range of 0.005 wt. % to 0.1 wt. %, based on the weight of the catalyst, such as 0.01 wt. % to 0.6 wt. % or 0.01 wt. % to 0.05 wt. %. When the dehydrogenation component comprises one or more metals of lesser dehydrogenation activity, e.g., one or more of Ga, In, Zn, Cu, Re, Mo, and W, a greater amount of dehydrogenation component is needed, e.g., in the range of 0.05 wt. % to 10 wt. %, based on the weight of the catalyst, such as 0.1 wt. % to 5 wt. % or 0.5 wt. % to 2 wt. %.

Besides the molecular sieve component and dehydrogenation component, the catalyst can further comprise an optional matrix component, e.g., one or more inorganic binders. A matrix component can be used, e.g., to make the catalyst more resistant to the temperatures and other conditions employed in the conversion reaction. The amount of matrix component is not critical. When present, the amount of matrix component is typically in the range of 0.01 times the weight of the molecular sieve component to about 0.9 times the weight of the molecular sieve component, e.g., in the range of 0.02 to 0.8. The matrix component can include active materials, such as synthetic or naturally occurring zeolites. Alternatively, or in addition, the matrix component can include clays and/or oxides such as alumina, silica, silica-alumina, zirconia, titania, magnesia, or mixtures of these and other oxides. The matrix component can include naturally occurring materials and/or materials in the form of gelatinous precipitates or gels including mixtures of silica and metal oxides. Clays may also be included with the oxide type binders to modify the mechanical properties of the catalyst or to assist in its manufacture. Alternatively, or in addition, the matrix component can include one or more substantially inactive materials. Inactive materials suitably serve as diluents to control the amount of conversion so that products may be obtained economically and orderly without employing other means for controlling the rate of reaction. Alternatively or in addition to any phosphorous added to or impregnated into the molecular sieve component, the matrix component can optionally include phosphorous, e.g., to lessen catalyst acidity. The matrix component is optional.

The catalyst can be one that has been subjected to one or more treatments, e.g., a selectivation treatment to increase selectivity for producing desired aromatic hydrocarbon compounds such as para-xylene. For example, the selectivation can be carried out before introduction of the catalyst into the reactor and/or in-situ in the reactor, e.g., by contacting (optionally a plurality of times) the catalyst with a selectivating agent, such as at least one organosilicon in a liquid carrier and subsequently calcining the catalyst at a temperature of 350 to 550° C. Such a selectivation process is described in detail in U.S. Pat. Nos. 5,633,417 and 5,675,047, which are incorporated by reference herein in their entirety.

Typically, the catalyst has a surface area as measured by nitrogen physisorption in the range of from 100 m$^2$/g to 600 m$^2$/g, e.g., in the range of from 200 m$^2$/g to 500 m$^2$/g. When the catalyst comprises aluminosilicate which includes phosphorous, the phosphorous:aluminum atomic ratio is typically in the range of from 0.01 to 0.5. For example, the catalyst can contain ≥10 wt. % of phosphorous-modified alumina, such as ≥15 wt. % or in the range of from 10 wt. % to 20 wt. %.

The dehydrocyclization is carried out in the presence of at least one of the specified dehydrocyclization catalysts, which is typically located in at least one bed within a dehydrocyclization reaction zone. Conventional fixed, moving, and/or fluidized beds can be used in the dehydrocyclization reaction zone, but the invention is not limited thereto.

During dehydrocyclization, at least a portion of the feed is exposed to a catalytically effective amount of the specified dehydrocyclization under catalytic dehydrocyclization conditions that are effective for converting at least a portion of the feed's $C_1$-$C_9$ non-aromatic hydrocarbon to aromatic hydrocarbon and molecular hydrogen. The catalytic dehydrocyclization conditions can include exposing the feed to a temperature in the range of from 400° C. to 650° C. and a pressure in the range of from 100 kPa to 2200 kPa. Typically, the catalytic dehydrocyclization conditions further include a space velocity (WHSV)≥0.1 hr$^{-1}$. More typically, the catalytic dehydrocyclization conditions include a temperature in the range of from 500° C. to 625° C. and a pressure in the range of from 30 psia (207 kPa) to 80 psia (522 kPa). Space velocity (WHSV) can be in the range of from 0.1 hr$^{-1}$ to 20 hr$^{-1}$. Typically, the space velocity (WHSV) of $C_{2+}$ hydrocarbon (the "$C_{2+}$ WHSV") in the specified raffinate with respect to the second catalyst is in the range of from 0.1 hr$^{-1}$ to 20 hr$^{-1}$, e.g., 0.2 hr$^{-1}$ to 5 hr$^{-1}$, or 0.3 hr$^{-1}$ to 1 hr$^{-1}$. The $C_{2+}$ WHSV is the hourly rate of the $C_{2+}$ hydrocarbon (in grams per hour) exposed to the second catalyst per gram of the second catalyst. The reaction is typically endothermic. Generally, the average temperature drop across the reaction zone is ≤600° C., more typically in the range of from 20° C. to 200° C., e.g., in the range of from 50° C. to 150° C.

Initial Separation Process for Separation of Aromatic Formation Effluent

As shown in FIG. 1, effluent from any of the foregoing aromatic formation processes can be conducted to a first separation process 120 for separation of one or more streams or fractions from the effluent. The initial or first separation process 120 can include one or more separation stages based on boiling point (distillation) differences within the effluent. Optionally, for feeds including a substantial portion of $C_{6+}$ alkane, a solvent separation stage may also be provided for separation of $C_{6+}$ alkane from $C_{6+}$ aromatic products.

Generally, the effluent from aromatic formation can include aromatic hydrocarbon, unreacted feed, and optionally additional non-aromatic reaction products. Most of the components in the effluent can be conveniently separated based on distillation methods, as shown in more detail in FIG. 2. The particular types of streams formed during separation can be dependent on the nature of the aromatic formation process and/or the nature of the separation stages.

In some aspects, the effluent from an aromatic formation process can include substantial amounts (such as more than 10 vol. %, or more than 20 vol. %) of $C_6$-$C_8$ aromatic hydrocarbon or $C_6$-$C_8$ aromatic hydrocarbon and $C_{9+}$ aromatic hydrocarbon. In such aspects, a distillation can allow for separation from the aromatic formation effluent of at least a $C_6$-$C_7$ aromatics stream, a $C_8$ aromatics stream, a (optional) $C_{9+}$ aromatics stream, optionally an unreacted feed stream and/or a hydrogen stream, and optionally one or more additional non-aromatic reaction product streams. Depending on the nature of the separation process, the $C_{9+}$ aromatics stream or another product stream can alternatively correspond to a remaining portion of the effluent after separation of other streams. The named aromatic hydrocarbon component ($C_6$-$C_7$; $C_8$; $C_{9+}$) for a stream corresponds to at least 50 wt. % of the aromatic hydrocarbon concentration in the stream, or at least 75 wt. % or at least 90 wt. %. The $C_8$ stream (or at least a portion of the $C_8$ stream) can be sent to a subsequent separation process for separation of a para-xylene enriched stream. The $C_6$-$C_7$ stream (or at least a portion of the $C_6$-$C_7$ stream) can be sent to a methylation process for conversion of at least a portion of the $C_6$-$C_7$ components to $C_8$ components. The $C_{9+}$ stream can be withdrawn from the reaction system, exposed to a dealkylation process to generate additional benzene for introduction into the methylation stage, exposed to a transalkylation process to generate additional $C_8$ aromatic hydrocarbon for introduction into the xylene separation process, and/or handled in any other convenient manner Optionally, a portion of the unreacted feed can be recycled to the aromatic formation process.

In other aspects, the output from the effluent from the aromatic formation process may contain substantial amounts of $C_6$-$C_7$ aromatic hydrocarbon, while having a reduced or minimized concentration of $C_8$ aromatic hydrocarbon and/or $C_{9+}$ aromatic hydrocarbon. In such aspects, a distillation can allow for separation from the aromatic formation effluent of at least a $C_6$ aromatics (i.e., benzene) stream, a $C_7$ aromatics stream, an unreacted feed stream and/or a hydrogen stream, and, optionally, a stream of non-aromatic reaction products. In yet other aspects, the effluent from the aromatic formation process may contain substantial amounts of $C_6$ aromatic hydrocarbon, unreacted feed, and hydrogen, while having a reduced or minimized amount of other aromatic components. In such aspects, the initial separation stage can separate at least a $C_6$ aromatics stream, an unreacted feed stream, and/or a hydrogen stream from the aromatic formation effluent.

Methylation of Aromatic Hydrocarbon

At least a portion of a $C_6$ stream, $C_7$ stream, or $C_6$-$C_7$ stream separated from the aromatic formation effluent in the first separation process can optionally be used as a product stream, as both benzene and toluene are commercially valuable. Another option can be to use at least a portion of a $C_6$ stream, $C_7$ stream, or $C_6$-$C_7$ stream separated from the aromatic formation effluent as a feed for a methylation process. A methylation process can form $C_8$ compounds by reacting $C_6$ and/or $C_7$ compounds with a methylating agent, such as methanol, dimethyl ether (DME), methyl bromide, and/or methyl chloride. Methylation processes typically provide a high selectivity for forming xylenes in preference to ethylbenzene. An example of a process for the selective production of para-xylene by exposing benzene and/or toluene to methanol under effective catalytic conditions is described in U.S. Pat. No. 8,344,197, which is incorporated herein by reference. Additionally, or alternately, a methylation process can be used for production of toluene from benzene.

Temperature is an important parameter in the reaction of benzene and/or toluene with a methylating agent. Because temperatures between 450° C. and 700° C. are beneficial for improving or maximizing conversion, the aromatic feed and methylating agent feed are preheated before being supplied to the methylation process, with the exothermic heat generated by the methylation reaction generally being sufficient to maintain the reaction temperature at the desired value. In practice, however, there are limits on the temperatures to which the different feeds can be preheated. For example, in the case of the benzene/toluene feed, the preheating temperature is limited by the coking rates in the preheater which, depending on factors such as heat flux, stream composition, and heat transfer surface metallurgy, will generally be about 550° C. In the case of the methylating agent feed, decomposition to carbon oxides, hydrogen and methane will generally limit the preheating temperature to about 220° C.

Generally, the conditions employed in a methylation process can include a temperature between 450° C. and 700° C. or about 550° C. to about 650° C.; a pressure between 14 psig and 1000 psig (between 100 and 7000 kPa), or between 10 psig and 200 psig (between 170 and 1480 kPa); a molar ratio of aromatic to methanol in the reactor charge of at least 0.2, such as from 2 to 20; and a weight hourly space velocity ("WHSV") for total hydrocarbon feed to the reactor(s) of 0.2 to 1000 hr$^{-1}$, or 0.5 to 500 hr$^{-1}$ for the aromatic reactant, and 0.01 to 100 hr$^{-1}$ for the methylating agent, based on total catalyst in the reactor(s).

The methylation process can employ any aromatic feedstock comprising toluene and/or benzene. Optionally, the aromatic feed can contain at least 90 weight %, especially at least 99 weight %, of benzene, toluene, or a mixture thereof. The composition of the methylating agent feed is not critical. Optionally, it can be beneficial to employ feeds containing at least 90 weight %, especially at least 99 weight %, of a methylating agent. The methylation process can produce a methylation effluent having a weight of $C_8$ aromatic hydrocarbon of at least 70% of a weight of $C_8$ aromatic hydrocarbon in the aromatic formation effluent, or at least 90%, or at least 100%, or at least 150%, or at least 200%.

The methylation catalyst can be a porous crystalline material, e.g., a medium-pore size aluminosilicate zeolite. Medium pore zeolites are generally defined as those having a pore size of about 5 to about 7 Angstroms, such that the zeolite freely sorbs molecules such as n-hexane, 3-methylpentane, benzene and p-xylene. Another common definition for medium pore zeolites involves the Constraint Index test which is described in U.S. Pat. No. 4,016,218, which is incorporated herein by reference. Medium pore zeolites typically have a Constraint Index of about 1-12, as measured on the zeolite alone without the introduction of oxide modifiers and prior to any steaming to adjust the diffusivity of the catalyst. In addition to the medium-pore size aluminosilicate zeolites, other medium pore acidic metallosilicates, such as silicoaluminophosphates (SAPOs), can be used in the present process.

Suitable medium pore zeolites include ZSM-5, ZSM-11, ZSM-12, ZSM-22, ZSM-23, ZSM-35, and ZSM-48, such as ZSM-5 and/or ZSM-11. The zeolite can be ZSM-5 having a silica to alumina molar ratio of at least 250, as measured prior to any treatment of the zeolite to adjust its diffusivity.

Second Separation Process

The methylation process 130 produces an effluent that can be separated in a second separation process 140 to form one or more output streams based on boiling point or distillation. In aspects where xylene production occurs (such as para-xylene production), a first output stream separated from a methylation effluent can be an unreacted $C_6$-$C_7$ stream (possibly including $C_7$ compounds that formed due to methylation of $C_6$), which can be at least partially recycled to the methylation. A second output stream separated from the methylation effluent can correspond to a lower boiling point stream, including unreacted methanol and other $C_{5-}$ reaction products. A third output stream separated from the methylation effluent can correspond to a $C_8$ aromatics stream. Optionally, one of the first output stream, second output stream, or third output stream can correspond to a remaining portion of the methylation effluent after separation of other output streams.

Third Separation Process (Xylene Separation)

Typically, distillation is not an effective method for separation of para-xylene from other xylenes and/or ethylbenzene. Instead, para-xylene is typically separated from a $C_8$ aromatic fraction or stream by other convenient methods, such as by selective adsorption or crystallization, as represented by third separation process 150 in FIG. 1. U.S. Pat. Nos. 5,750,820 and 8,529,757 (each of which is incorporated herein by reference in its entirety) describe selective adsorption methods which can be referred to as a simulated moving bed.

The description below describes operation of a simulated moving bed based on the simple conceptual example of having a number of zones equal to the minimum number needed to show the different simulated moving bed processes at the same time. Those of skill in the art will recognize that more generally any number of zones can be included in a simulated moving bed separator. Generally, any convenient number of feed and/or output locations can be provided for the simulated moving bed. During operation, the different input streams and output streams for the simulated moving bed can be rotated through the feed and/or output locations to simulate the effect of having a moving bed separator.

In aspects where $C_8$ aromatic streams or fractions of varying para-xylene concentration are available, the $C_8$ output streams can be introduced into the simulated moving bed as separate feeds at different relative locations. For example, the effluent from the xylene isomerization process can be introduced into a simulated moving bed at a conventional location (the first location), e.g., downstream (with respect to fluid flow) of the location (the second location) at which purified para-xylene is extracted from the simulated moving bed. For the $C_8$ streams derived from the aromatic formation effluent and/or the methylation effluent, one or more input locations that are positioned between the first and second location can be selected, e.g., based on the para-xylene concentration of each respective effluent. This can optionally allow the $C_8$ stream separated from the aromatic formation effluent and/or the methylation effluent to be introduced into the simulated moving bed separator at a location where the para-xylene concentration in the fluid undergoing separation in the simulated moving bed at the input location approximately corresponds to the para-xylene concentration in the aromatic formation effluent or methylation effluent. This decreases or even minimizes separator volume, as the $C_8$ streams with higher para-xylene concentration can be introduced at locations in the simulated moving bed which are relatively close to the location at which purified para-xylene is extracted. Advantageously, doing so lessens the volume of input flows with lower para-xylene purity, which would otherwise lead to a need for increased bed volume and/or energy for para-xylene separation.

Crystallization methods can be used to separate para-xylene from a $C_8$ aromatic starting material which contains ethylbenzene, as well as the three xylene isomers. Para-xylene has a freezing point of 13.3° C., meta-xylene has a freezing point of −47.9° C., and ortho-xylene has a freezing point of −25.2° C.

Crystallization processes typically use feed mixture cooling to recover para-xylene from a mixture of $C_8$ aromatics. Because its melting point is much higher than that of the other $C_8$ aromatics, para-xylene is readily separated in the crystallizer after refrigeration of the stream. In conventional para-xylene crystallization processes, the feed contains about 22 to about 23 wt. % para-xylene. This is the type of feed that is generally obtained from xylene isomerization and non-shape selective toluene disproportionation processes, in which the relative proportion of xylene isomers is close to equilibrium at reaction temperatures. For the production of high purity para-xylene (≥99.5 to ≥99.8 wt. %) the feeds are cooled, crystallized, and separated at a cryogenic temperature, normally −65° C. to −70.5° C. In order to recover most of the para-xylene from solution, the feeds may need additional cooling, e.g., to about −85° C. to −95° C. The crystals are melted, and the resulting solution is recrystallized and separated at a warmer temperature for increased para-xylene purity.

Conventional xylene separation processes can be used, but the invention is not limited thereto. Suitable separation processes are described in U.S. Pat. Nos. 5,750,820; 7,989,762; and 8,529,757; which are incorporated by reference herein in their entirety.

Xylene Isomerization

Typically xylene streams found in chemical or petrochemical plants also contain ethylbenzene. Conventional isomerization technologies operating at high temperatures (e.g., 400° C.) in vapor phase isomerize the xylenes and dealkylate ethylbenzene to benzene. Other vapor-phase isomerization technologies convert ethylbenzene to xylenes in addition to xylenes isomerization. There are also liquid-phase isomerization technologies.

For the methods described herein, both vapor phase isomerization and liquid phase isomerization can be suitable for isomerization of the para-xylene depleted stream from a para-xylene separation process. For aromatic formation processes other than pyrolysis, a $C_8$ aromatics stream separated from the aromatic formation process can have a reduced ethylbenzene concentration. In some aspects, the reduced amount of ethylbenzene in $C_8$ aromatics streams separated from an aromatic formation effluent and/or methylation effluent can allow for reduced severity during vapor phase isomerization. In some aspects, the reduced amount of ethylbenzene in $C_8$ aromatic streams separated from the aromatic formation effluent and/or methylation effluent can allow for use of liquid phase isomerization for some or all of the isomerization of the para-xylene depleted stream from the para-xylene separation stage.

U.S. Pat. No. 8,697,929 describes an example of a liquid phase isomerization system, the entirety of which is incorporated herein by reference. Briefly, liquid phase isomerization of xylenes can be performed at a temperature of less than 295° C. and a pressure sufficient to maintain the xylenes in liquid phase. In embodiments, the process utilizes a catalyst comprising a zeolite, preferably at least one selected from the group consisting of ZSM-5 and MCM-49. In embodiments, the process utilizes a catalyst comprising ZSM-5 along with a binder or the ZSM-5 may be self-bound. Optionally, the catalyst can be characterized by one or more of the following characteristics: the ZSM-5 is in the proton form (HZSM-5); the ZSM-5 has a crystal size of less than 0.1 microns; the ZSM-5 has a mesoporous surface area (MSA) greater than 45 $m^2/g$; the ZSM-5 has a zeolite surface area (ZSA) to mesoporous surface area (MSA) ratio of less than 9; or a silica to alumina weight ratio in the range of 20 to 50.

In aspects, very low level of by-products are produced, such as less than 1 wt. % or preferably less than 0.5 wt. % of by-products selected from non-aromatic compounds, benzene and $C_{9+}$ aromatic hydrocarbon, and mixtures thereof.

The liquid phase isomerization process comprises contacting a feedstream comprising $C_8$ aromatic hydrocarbons with a catalyst suitable for isomerization at a temperature below 295° C., preferably below 280° C., and at a pressure sufficiently to keep the reactant in liquid phase. One of skill in the art would be able to determine other operating characteristics, such as a lower temperature, within which the present invention may be practiced. Lower limits may be, for instance, above 180° C. or 190° C. or 200° C., or 210° C., and the like. The flow rate can be selected by one of ordinary skill in the art in possession of the present disclosure, but may advantageously be selected within the range from 1 to 100 WHSV, preferably from 1 to 20 WHSV, and more preferably from 1 to 10 WHSV.

Although the invention has been described and illustrated with respect to certain aspects, it is to be understood that the invention is not limited to the particulars disclosed and extends to all equivalents within the scope of the claims. Unless otherwise stated, all percentages, parts, ratios, etc., are by weight. Unless otherwise stated, a reference to a compound or component includes the compound or component by itself as well as in combination with other elements, compounds, or components, such as mixtures of compounds. Further, when an amount, concentration, or other value or parameter is given as a list of upper preferable values and lower preferable values, this is to be understood as specifically disclosing all ranges formed from any pair of an upper preferred value and a lower preferred value, regardless of whether ranges are separately disclosed. All patents, test procedures, and other documents cited herein, including priority documents, are fully incorporated by reference to the extent such disclosure is not inconsistent and for all jurisdictions in which such incorporation is permitted.

The invention claimed is:

1. A method for forming aromatic compounds, comprising:
providing a feed comprising a non-aromatic hydrocarbon, at least a portion of the non-aromatic hydrocarbon being obtained from each of a recycle portion of a first light ends stream and a recycle portion of a second light ends stream;
aromatizing at least a portion of the feed's non-aromatic hydrocarbon to produce an aromatic formation effluent comprising benzene, a $C_7$ aromatic hydrocarbon, and a $C_8$ aromatic hydrocarbon, the aromatization being carried out in an aromatic formation process under effective aromatic formation conditions;
separating from the aromatic formation effluent a first higher boiling intermediate stream, a first lower boiling intermediate stream, and a first light ends stream which includes the recycle portion of the first light ends stream, wherein the first higher boiling intermediate stream has a $C_7$ aromatic hydrocarbon concentration (weight percent), a $C_8$ aromatic hydrocarbon concentration (weight percent) or a combined $C_7$-$C_8$ aromatic hydrocarbon concentration (weight percent) greater than those of the aromatic formation effluent, wherein the first lower boiling intermediate stream has a benzene concentration (weight percent), a $C_7$ aromatic hydrocarbon concentration (weight percent) or a combined $C_6$-$C_7$ aromatic hydrocarbon concentration (weight percent) greater than those of the aromatic formation effluent, and wherein the first light ends stream comprises a $C_2$-$C_5$ hydrocarbon;
methylating at least a portion of the first lower boiling intermediate stream with a methylating agent to form a methylated intermediate stream, the methylated intermediate stream having a $C_7$-$C_8$ aromatic hydrocarbon concentration (weight percent) greater than that of the portion of the first lower boiling intermediate stream which reacts to form the methylated intermediate stream;
separating from the methylated intermediate stream a second higher boiling intermediate stream, a second lower boiling intermediate stream, and a second light ends stream which includes the recycle portion of the second light ends stream, wherein the second higher boiling intermediate stream has a $C_7$-$C_8$ aromatic hydrocarbon concentration (weight percent) greater than that of the methylated intermediate stream, and wherein the second light ends stream comprises a $C_2$-$C_5$ hydrocarbon;
and
transferring the recycle portion of the first light ends stream and the recycle portion of the second light ends stream to the feed.

2. The method of claim 1, the method further comprising:
separating a first para-xylene enriched fraction and a first para-xylene depleted fraction from the first higher boiling intermediate stream, the first para-xylene enriched fraction having a para-xylene concentration (weight percent) greater than that of the first higher boiling intermediate stream;
separating a second para-xylene enriched fraction and a second para-xylene depleted fraction from the second higher boiling intermediate stream, the second para-xylene enriched fraction having a para-xylene concentration (weight percent) greater than that of the second higher boiling intermediate stream;

isomerizing at least a portion of the first para-xylene depleted fraction, the second para-xylene depleted fraction, or a combination thereof to form an isomerized product stream, wherein the portion of the first para-xylene depleted fraction, the second para-xylene depleted fraction, or a combination thereof subjected to the isomerization has a para-xylene concentration (weight percent) less than that of the isomerized product stream; and separating a third para-xylene enriched fraction from the isomerized product stream, the third para-xylene enriched fraction having a para-xylene concentration (weight percent) greater than that of the isomerized product stream.

3. The method of claim 1, wherein the separating from the aromatic formation effluent a first higher boiling intermediate stream, a first lower boiling intermediate stream, and a first light ends stream comprises:

separating from the aromatic formation effluent a hydrogen-containing stream comprising at least 50 wt. % of methane, hydrogen, and carbon oxides relative to a weight of the hydrogen-containing stream and a demethanized stream comprising the first higher boiling intermediate stream, the first lower boiling intermediate stream, and the first light ends stream;

separating from the demethanized stream a demethanized aliphatic hydrocarbon stream comprising the first light ends stream and an aromatics-containing stream comprising the first higher boiling intermediate stream and the first lower boiling intermediate stream, the demethanized aliphatic hydrocarbon stream being enriched in $C_2$-$C_3$ hydrocarbons relative to the demethanized stream; and separating from at least a portion of the aromatics-containing stream the first higher boiling intermediate stream and the first lower boiling intermediate stream.

4. The method of claim 1, wherein separating from the aromatic formation effluent a first higher boiling intermediate stream, a first lower boiling intermediate stream, and a first light ends stream comprises:

separating an aromatics-containing stream and an aliphatic hydrocarbon stream from the aromatic formation effluent;

separating from at least a portion of the aromatics-containing stream the first higher boiling intermediate stream and the first lower boiling intermediate stream; and separating from the aliphatic hydrocarbon stream a hydrogen-containing stream comprising at least 50 wt. % of methane, hydrogen, and carbon oxides relative to a weight of the hydrogen-containing stream and a demethanized aliphatic hydrocarbon stream comprising the first light ends stream, the demethanized aliphatic hydrocarbon stream being enriched in $C_2$-$C_3$ hydrocarbons relative to the aliphatic hydrocarbon stream.

5. The method of claim 4, wherein the demethanized aliphatic hydrocarbon stream is enriched in $C_2$-$C_5$ hydrocarbons relative to at least one of the demethanized stream and the aliphatic hydrocarbon stream.

6. The method of claim 1, wherein the first lower boiling intermediate stream is a $C_6$ aromatics stream, and/or wherein the second higher boiling intermediate stream is a $C_7$ aromatics stream.

7. The method of claim 1, wherein the effective aromatic formation conditions comprise conversion of less than 10 wt. % of methane relative to a weight of methane in the feed.

8. The method of claim 1, further comprising separating at least a portion of the second light ends stream and a stream comprising dimethyl ether from the second light ends stream.

9. The method of claim 1, further comprising separating a deoxygenated light ends stream and a stream comprising dimethyl ether from the second light ends stream; and separating the recycle portion of the second light ends stream from the deoxygenated light ends stream.

10. The method of claim 1, wherein the recycle portion of the second light ends stream comprises a $C_2$-$C_3$ olefin stream, a $C_2$-$C_3$ hydrocarbon stream, or a combination thereof.

11. The method of claim 1, wherein the aromatic formation effluent comprises≤20 wt. % of $C_8$ aromatic hydrocarbon.

12. The method of claim 1, wherein the first lower boiling intermediate stream is a $C_6$-$C_7$ aromatics stream.

13. The method of claim 1, wherein the first lower boiling intermediate stream is a $C_7$ aromatics stream, the method further comprising separating a $C_6$ aromatics stream from the aromatic formation effluent.

14. The method of claim 1, wherein the aromatic formation process includes at least one of (a) less than 5 wt. % of the non-aromatic hydrocarbon converted in the aromatic formation process is methane, (b) at least 10 wt. % of the non-aromatic hydrocarbon converted in the aromatic formation process is ethane, (c) at least 20 wt. % of the non-aromatic hydrocarbon converted in the aromatic formation process is $C_1$-$C_4$ alkane, and (d) 50 wt. % or less of the non-aromatic hydrocarbon converted in the aromatic formation process is $C_5$-$C_9$ alkane.

15. The method of claim 1, wherein (a) the feed's non-aromatic hydrocarbon comprises $C_1$-$C_9$ alkane, and the aromatic formation process includes converting at least 20 wt. % of the feed's $C_1$-$C_9$ alkane; (b) the feed's non-aromatic hydrocarbon comprises $C_1$-$C_4$ alkane, and the aromatic formation process includes converting at least 20 wt. % of the feed's $C_1$-$C_4$ alkane; (c) the feed's non-aromatic hydrocarbon comprises $C_1$-$C_2$ alkane, and the aromatic formation process includes converting at least 20 wt. % of the feed's $C_1$-$C_2$ alkane; (d) the feed's non-aromatic hydrocarbon comprises ethane, and the aromatic formation process includes converting at least 10 wt. % of the feed's ethane; or (e) the feed's non-aromatic hydrocarbon comprises methane, and the aromatic formation process includes converting at least 10 wt. % of the feed's methane.

16. The method of claim 1, wherein the feed's non-aromatic hydrocarbon comprises ≥95 wt. % of $C_1$-$C_9$ alkane, and the feed includes less than 0.2 moles of methane per mole of $C_1$-$C_9$ alkane.

17. The method of claim 1, further comprising converting methane to synthesis gas and/or methanol, wherein the formation of the methylated intermediate stream is carried out in the presence of at least a portion of the converted synthesis gas and/or methanol, at least a portion of the converted synthesis gas and/or methanol optionally being a co-feed to the aromatic formation process.

18. The method of claim 1, further comprising:

combining at least the recycle portion of the first light ends stream with at least the recycle portion of the second light ends stream to form a combined light ends stream; and transferring the combined light ends stream comprising the recycle portion of the first light ends stream and the recycle portion of the second light ends stream to the feed.

19. A method for forming aromatic compounds, comprising:
providing a feed comprising a non-aromatic hydrocarbon, the non-aromatic hydrocarbon comprising a recycle portion of a first light ends stream and a recycle portion of a second light ends stream;
producing an aromatic formation effluent comprising benzene, a $C_7$ aromatic hydrocarbon, and a $C_8$ aromatic hydrocarbon from at least a portion of the feed's non-aromatic hydrocarbon in an aromatic formation process carried out under effective aromatic formation conditions;
separating from the aromatic formation effluent a first $C_8$ intermediate stream, a first lower boiling intermediate stream, a hydrogen-containing stream, and the first light ends stream, wherein the first $C_8$ intermediate stream has a $C_8$ aromatic hydrocarbon concentration (weight percent) greater than that of the aromatic formation effluent, wherein the first lower boiling intermediate stream has a benzene concentration (weight percent), a $C_7$ aromatic hydrocarbon concentration (weight percent), or a combined $C_6$-$C_7$ aromatic hydrocarbon concentration (weight percent) greater than those of the aromatic formation effluent, wherein the first light ends stream comprises a $C_2$-$C_5$ hydrocarbon, and wherein the separation of the hydrogen-containing stream comprising separating uses a cooling system comprising $C_1$-$C_4$ refrigerant;
catalytically reacting at least a portion of the first lower boiling intermediate stream with a methylating agent to form a methylated intermediate stream, the methylated intermediate stream having a $C_8$ aromatic hydrocarbon concentration (weight percent) greater than that of the portion of the first lower boiling intermediate stream which reacts to form the methylated intermediate stream;
separating from the methylated intermediate stream a second $C_8$ intermediate stream, a second lower boiling intermediate stream, and the second light ends stream, the second $C_8$ intermediate stream having a $C_8$ aromatic hydrocarbon concentration (weight percent) greater than that of the methylated intermediate stream;
separating the recycle portion of the first light ends stream from at least a portion of the first light ends stream; and
separating the recycle portion of the second light ends stream from at least a portion of the second light ends stream, wherein
   i) the method further comprises separating a deoxygenated light ends stream and a stream comprising dimethyl ether from the second light ends stream, the deoxygenated light ends stream comprising the at least a portion of the second light ends stream, wherein the separation of the stream comprising dimethyl ether from the second light ends stream includes separating using the cooling system comprising the $C_1$-$C_4$ refrigerant;
   ii) the method further comprises:
      separating a first para-xylene enriched fraction and a first para-xylene depleted fraction from the first $C_8$ intermediate stream, the first para-xylene enriched fraction having a para-xylene concentration (weight percent) greater than that of the first $C_8$ intermediate stream; and
      separating a second para-xylene enriched fraction and a second para-xylene depleted fraction from the second $C_8$ intermediate stream, the second para-xylene enriched fraction having a para-xylene concentration (weight percent) greater than that of the second $C_8$ intermediate stream,
      wherein at least one of 1) the separating a first para-xylene enriched fraction and a first para-xylene depleted fraction from the first $C_8$ intermediate stream, and 2) the separating a second para-xylene enriched fraction and a second para-xylene depleted fraction from the second $C_8$ intermediate stream, comprises separating using the cooling system comprising the C1-C4 refrigerant; or
   iii) a combination of i) and ii).

20. The method of claim 19, further comprising exposing the second $C_8$ intermediate stream to hydrogen separated from at least a portion of the hydrogen-containing stream in the presence of a hydrogenation catalyst to at least partially saturate the second $C_8$ intermediate stream.

21. The method of claim 19, wherein the cooling system comprises a $C_2$-$C_3$ refrigerant.

22. The method of claim 19, further comprising:
combining at least a portion of the first light ends stream with at least a portion of the second light ends stream to form a combined light ends stream; and
separating the recycle portion of the first light ends stream and the recycle portion of the second light ends stream from the combined light ends stream.

23. A method for forming aromatic compounds, comprising:
providing a feed comprising non-aromatic hydrocarbon, the non-aromatic hydrocarbon comprising a recycle portion of a first light ends stream and a recycle portion of a second light ends stream;
producing an aromatic formation effluent comprising benzene, a $C_7$ aromatic hydrocarbon, and a $C_8$ aromatic hydrocarbon from at least a portion of the feed's non-aromatic hydrocarbon in an aromatic formation process carried out under effective aromatic formation conditions;
separating from the aromatic formation effluent a first $C_8$ intermediate stream, a first lower boiling intermediate stream, a hydrogen-containing stream, and the first light ends stream, wherein the first $C_8$ intermediate stream has a $C_8$ aromatic hydrocarbon concentration (weight percent) greater than that of the aromatic formation effluent, wherein the first lower boiling intermediate stream has a benzene concentration (weight percent), a $C_7$ aromatic hydrocarbon concentration (weight percent), or a combined $C_6$-$C_7$ aromatic hydrocarbon concentration (weight percent) greater than those of the aromatic formation effluent, and wherein the first light ends stream comprises a $C_2$-$C_5$ hydrocarbon;
reacting at least a portion of the first lower boiling intermediate stream with a methylating agent in the presence of a zeolite catalyst to form a methylated intermediate stream, the methylated intermediate stream having a $C_8$ aromatic hydrocarbon concentration (weight percent) greater than that of the portion of the first lower boiling intermediate stream which reacts to form the methylated intermediate stream;
separating from the methylated intermediate stream a second $C_8$ intermediate stream, a second lower boiling intermediate stream, and the second light ends stream, wherein the second $C_8$ intermediate stream comprises styrene and has a $C_8$ aromatic hydrocarbon concentration (weight percent) greater than that of the methylated intermediate stream, and wherein the second light ends stream comprises a $C_2$-$C_5$ hydrocarbon;

exposing the second $C_8$ intermediate stream to hydrogen separated from at least a portion of the hydrogen-containing stream in the presence of a hydrogenation catalyst to at least partially saturate unsaturated alkyl side chains in the second $C_8$ intermediate stream;

separating a first para-xylene enriched fraction and a first para-xylene depleted fraction from the first $C_8$ intermediate stream, the first para-xylene enriched fraction having a para-xylene concentration (weight percent) greater than that of the first $C_8$ intermediate stream;

separating a second para-xylene enriched fraction and a second para-xylene depleted fraction from the second $C_8$ intermediate stream, the second para-xylene enriched fraction having a para-xylene concentration (weight percent) greater than that of the second $C_8$ intermediate stream;

isomerizing at least a portion of the first para-xylene depleted fraction, the second para-xylene depleted fraction, or a combination thereof to form an isomerized product stream, wherein the portion of the first para-xylene depleted fraction, the second para-xylene depleted fraction, or a combination thereof subjected to the isomerization has a para-xylene concentration (weight percent) less than that of the isomerized product stream;

separating a third para-xylene enriched fraction from the isomerized product stream, the third para-xylene enriched fraction having a para-xylene concentration (weight percent) greater than that of the isomerized product stream;

separating the recycle portion of the first light ends stream from at least a portion of the first light ends stream; and separating the recycle portion of the second light ends stream from at least a portion of the second light ends stream.

24. The method of claim 23, further comprising separating the at least a portion of the first light ends stream and a stream comprising methane from the first light ends stream.

25. The method of claim 24, wherein the stream comprising methane comprises the hydrogen-containing stream.

26. The method of claim 23, wherein the at least a portion of the first light ends stream comprises a $C_1$-$C_5$ hydrocarbon stream or a $C_2$-$C_5$ hydrocarbon stream.

* * * * *